United States Patent
Landry et al.

(10) Patent No.: US 12,011,372 B2
(45) Date of Patent: Jun. 18, 2024

(54) LOCKING PROSTHETIC KNEE AND CORE COMPONENTS THEREFOR

(71) Applicant: Össur Iceland ehf, Reykjavik (IS)

(72) Inventors: David Landry, Reykjavik (IS); Gudni Ingimarsson, Reykjavik (IS); Gunnar Omar Lillie Magnusson, Reykjavik (IS); Lucas Ikelaar, Reykjavik (IS); Sylvain Gagné, Reykjavik (IS)

(73) Assignee: Össur Iceland ehf, Reykjavik (IS)

( * ) Notice: Subject to any disclaimer, the term of this patent is extended or adjusted under 35 U.S.C. 154(b) by 155 days.

(21) Appl. No.: 17/685,215

(22) Filed: Mar. 2, 2022

(65) Prior Publication Data
US 2022/0280316 A1    Sep. 8, 2022

Related U.S. Application Data

(60) Provisional application No. 63/200,378, filed on Mar. 3, 2021.

(51) Int. Cl.
*A61F 2/64* (2006.01)
*A61F 2/50* (2006.01)
(Continued)

(52) U.S. Cl.
CPC .......... *A61F 2/64* (2013.01); *A61F 2/70* (2013.01); *A61F 2/74* (2021.08);
(Continued)

(58) Field of Classification Search
CPC ...... A61F 2/64; A61F 2/74; A61F 2/70; A61F 2002/5043; A61F 2002/6854; A61F 2002/6863
See application file for complete search history.

(56) References Cited

U.S. PATENT DOCUMENTS

| | | | |
|---|---|---|---|
| 1,124,220 A | * | 1/1915 | Gaines ............... A61F 2/64 403/162 |
| 6,610,101 B2 | | 8/2003 | Herr et al. |

(Continued)

FOREIGN PATENT DOCUMENTS

DE    190483 C    10/1907

OTHER PUBLICATIONS

International Search Report and Written Opinion in PCT/IB2022/051816 dated Jul. 7, 2022 in 17 pages.

*Primary Examiner* — Jerrah Edwards
*Assistant Examiner* — Maximilian Tobias Spencer
(74) *Attorney, Agent, or Firm* — Knobbe, Martens, Olson & Bear, LLP

(57) ABSTRACT

A prosthetic knee can include a variable-torque magneto-rheological (MR) actuator assembly or braking system, a frame and an electronics assembly or system that also serves as a mount for the knee actuator and facilitates in monitoring and controlling the operation of the knee actuator. The prosthetic knee system advantageously provides resistive forces to substantially simulate the position and motion of a natural knee joint during ambulation and/or other locomotory activities performed by the amputee. The prosthetic knee can have a series of internal blades for providing resistive forces. A locking ratchet can be used to lock knee position. A dynamic seal with a protective shim can be disposed in the knee actuator. A coil with a non-circular cross-section can be used.

19 Claims, 24 Drawing Sheets

(51) Int. Cl.
*A61F 2/68* (2006.01)
*A61F 2/70* (2006.01)
*A61F 2/74* (2006.01)

(52) U.S. Cl.
CPC ............... *A61F 2002/5043* (2013.01); *A61F 2002/6854* (2013.01); *A61F 2002/6863* (2013.01)

(56) References Cited

U.S. PATENT DOCUMENTS

| | | |
|---|---|---|
| 6,764,520 B2 | 7/2004 | Deffenbaugh et al. |
| 7,101,487 B2 | 9/2006 | Hsu et al. |
| 7,198,071 B2 | 4/2007 | Bisbee, III et al. |
| 7,455,696 B2 | 11/2008 | Bisbee, III et al. |
| 7,691,154 B2 | 4/2010 | Asgeirsson et al. |
| 8,435,309 B2 | 5/2013 | Benoit et al. |
| 2006/0069449 A1* | 3/2006 | Bisbee, III ............... A61F 2/64 623/46 |
| 2006/0074493 A1 | 4/2006 | Bisbee, III et al. |
| 2006/0136072 A1 | 6/2006 | Bisbee et al. |
| 2009/0299480 A1* | 12/2009 | Gilbert ............... A61F 5/0125 623/18.11 |

* cited by examiner

LOCKING PROSTHETIC KNEE AND CORE COMPONENTS THEREFOR

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present invention relates to prosthetic devices in general and, in particular, to magnetorheologically actuated controllable braking systems utilized in prosthetic knees.

Description of the Related Art

Three types of variable-torque brakes have been employed in prosthetic knees in the past: (i) dry friction brakes where one material surface rubs against another surface with variable force; (ii) viscous torque brakes using a hydraulic fluid squeezed through a variable sized orifice or flow restriction plate; and (iii) magnetorheological (MR) brakes or dampers where MR fluid (containing small iron particles suspended in the fluid) is squeezed through a fixed orifice or flow restriction plate, with viscosity of the fluid being varied in response to an applied magnetic field. Each of these technologies, as conventionally practiced in the field of prosthetics, can pose certain disadvantages.

Though dry friction brakes can generally provide a substantial torque range for their size, undesirably, they are often difficult to control. After extended use, the frictional pads tend to wear, thereby changing the frictional characteristics of the brake and the torque response for a given commanded torque. Disadvantageously, this can cause unreliable damping performance, and hence adversely affect the gait of the amputee and also cause discomfort to the amputee. Consequently, dry friction brakes may need frequent servicing and/or replacement which undesirably adds to the cost.

Under high loading conditions, viscous torque brakes are susceptible to leakage of hydraulic fluid and possibly other damage due to excessive pressure build-up. Disadvantageously, this can result in an irreversible state, since once the brake unit is overloaded it cannot return to normal. Therefore, such a viscous torque brake for a prosthetic joint is prone to catastrophic failure, and hence can be unreliable and detrimental to the safety of an amputee.

In certain MR brakes and dampers, the interaction of the MR fluid with the device undesirably causes increased pressure, seal deterioration, or a combination of the two. Another possible cause of these adverse effects is decomposition of the MR fluid. Once the seals fail or the MR fluid decomposes, the prosthetic knee is no longer suitable for use.

SUMMARY

In accordance with one aspect of the disclosure, a prosthetic knee is provided with a magnetorheological fluid actuator movably coupled to a shank of the prosthetic knee. The MR actuator has a plurality of blades spaced apart from each other by spacers and frictionally coupled to a core shank. The MR actuator advantageously reduces mechanical play between the blades and the core shank, thereby reducing wear and tear of the MR actuator.

In accordance with an aspect of the disclosure, a prosthetic knee is provided with a distal shank and a proximal actuator that rotates relative to the shank. The prosthetic knee includes a mechanical lock mechanism actuatable (manually by a user) to selectively lock the actuator in one or more positions relative to the shank of the prosthetic knee. For example, the actuator can be locked relative to the shank in a first position corresponding to a user standing straight, in a second position corresponding to a user with their knee slightly bent, and a third position corresponding to the user with their knee further bent such as for sitting on a bar stool.

In accordance with an aspect of the disclosure, a prosthetic knee is provided with a magnetorheological fluid actuator movably coupled to a shank of the prosthetic knee. The MR actuator includes a coil defined by windings having a non-circular cross-sectional profile. The windings can have a cross-section with one or more linear edges, such as a square or rectangular cross-section, allowing the windings to be arranged so that a linear edge of one winding is adjacent a linear edge of an adjacent winding, thereby providing a more compact winding arrangement. In some embodiments, the windings can be produced by flattening a wire with an originally circular cross section. The windings can be rectangular with round edges. The more compact winding arrangement advantageously reduces open space between windings, resulting in increased a magnetic field with the same volume of coil because more windings can be filled into the same space.

In accordance with an aspect of the disclosure, a prosthetic knee is provided with a magnetorheological fluid actuator movably coupled to a shank of the prosthetic knee. The MR actuator includes dynamic seals that include a seal cavity filled with grease to inhibit (e.g., prevent) iron particles from the MR fluid from contacting the seal. A seal protector shim is disposed between the seal and the outer spline of the actuator to provide a barrier between the grease and the MR fluid.

In accordance with one aspect of the disclosure, a prosthetic knee with an elongate frame configured to house electronics and a magnetorheological fluid actuator movably coupled to a proximal portion of the elongate frame, the actuator rotatable in an anterior-posterior direction about a medial-lateral axis is provided. The actuator can have an outer spline, a core extending from a first plate attached to the core and a second plate. The second plate can be removably couplable to an opposite end of the core from the first plate. The actuator can further include a coil disposed about the core, and a collar disposed about the coil. The coil can be coupled to the first and second plates. The collar can have a continuous outer surface with an outer dimension. The actuator can further include a first plurality of annular blades, the first plurality of blades slidable over the collar and having an opening with an inner dimension approximately equal to the outer dimension of the collar. The actuator can also have a second plurality of annular blades slidable over the collar. The second plurality of annular blades can have a toothed outer edge that define one or more teeth configured to engage with a splined surface of the outer spline. Each of the second plurality of annular blades can alternate with and be separated from each of the first plurality of annular blades by a gap containing a magnetorheological fluid. The first plurality of annular blades can be clamped between the first and second plates. The actuator can have a proximal connector coupled to the outer spline and configured to rotate with the outer spline about the medial-lateral axis, and a distal connector coupled to a distal end of the elongate frame. A torsional resistance of the actuator to rotation about the medial-lateral axis can vary based on a magnitude of a magnetic field applied by the coil to the magnetorheological fluid to vary the viscosity of the MR fluid in the actuator.

In accordance with another aspect of the disclosure, a prosthetic knee, with an elongate frame configured to house electronics and a magnetorheological fluid actuator movably coupled to a proximal portion of the elongate frame, the actuator rotatable in an anterior-posterior direction about a medial-lateral axis is provided. The actuator can have an outer spline, and a core. The actuator can further include a lock assembly operable to lock the actuator relative to the frame in one or more extension positions. The lock assembly can have one or more teeth on the outer spline, the one or more teeth can be configured to releasably engage a locking blade to lock the actuator. The blade can have a hook that engages the one or more teeth. The prosthetic knee can further include a coil, a proximal connector coupled to the outer spline and configured to rotate with the outer spline about the medial-lateral axis; and a distal connector coupled to a distal end of the elongate frame. A torsional resistance of the actuator to rotation about the medial-lateral axis can vary based on a magnitude of a magnetic field applied by the coil to the magnetorheological fluid to vary the viscosity of the MR fluid in the actuator.

In accordance with another aspect of the disclosure, a prosthetic knee, with an elongate frame configured to house electronics and a magnetorheological fluid actuator movably coupled to a proximal portion of the elongate frame, the actuator rotatable in an anterior-posterior direction about a medial-lateral axis is provided. The actuator can have an outer spline, and a core. The prosthetic knee can further include a coil, a proximal connector coupled to the outer spline and configured to rotate with the outer spline about the medial-lateral axis; and a distal connector coupled to a distal end of the elongate frame. A torsional resistance of the actuator to rotation about the medial-lateral axis can vary based on a magnitude of a magnetic field applied by the coil to the magnetorheological fluid to vary the viscosity of the MR fluid in the actuator.

In accordance with another aspect of the disclosure, a prosthetic knee is provided. The prosthetic knee comprises an elongate frame configured to house electronics, and a magnetorheological (MR) fluid actuator movably coupled to a proximal portion of the elongate frame, the actuator rotatable in an anterior-posterior direction about a medial-lateral axis, the actuator comprising an outer spline and a core assembly. The prosthetic knee also comprises a lock assembly operable to lock the actuator relative to the frame in one or more extension positions. The lock assembly comprises a blade and one or more teeth on the outer spline configured to releasably engage the blade to lock the actuator, the blade having a hook that engages the one or more teeth. The prosthetic knee also comprises a coil, a proximal connector coupled to the outer spline and configured to rotate with the outer spline about the medial-lateral axis, and a distal connector coupled to a distal end of the elongate frame. A torsional resistance of the actuator to rotation about the medial-lateral axis varies based on a magnitude of a magnetic field applied by the coil to the magnetorheological fluid to vary the viscosity of the MR fluid in the actuator.

In accordance with another aspect of the disclosure, a prosthetic knee is provided. The prosthetic knee comprises an elongate frame configured to house electronics, and a magnetorheological (MR) fluid actuator movably coupled to a proximal portion of the elongate frame, the actuator rotatable in an anterior-posterior direction about a medial-lateral axis, the actuator comprising an outer spline and a core assembly. The prosthetic knee also comprises a coil comprising one or more wire portions, each wire portion having a transverse cross-section defined by one or more linear surfaces configured to be adjacent a linear surface of an adjacent wire portion. The prosthetic knee also comprises a proximal connector coupled to the outer spline and configured to rotate with the outer spline about the medial-lateral axis, and a distal connector coupled to a distal end of the elongate frame. A torsional resistance of the actuator to rotation about the medial-lateral axis varies based on a magnitude of a magnetic field applied by the coil to the magnetorheological fluid to vary the viscosity of the MR fluid in the actuator.

DETAILED DESCRIPTION

Understanding normal human walking/running provides the basis for the design and development of effective lower limb prostheses with controlled motion. Normal human locomotion or gait can be described as a series of rhythmical alternating movements of the limbs and trunk which result in the forward progression of the body's center of gravity.

Figure 1:
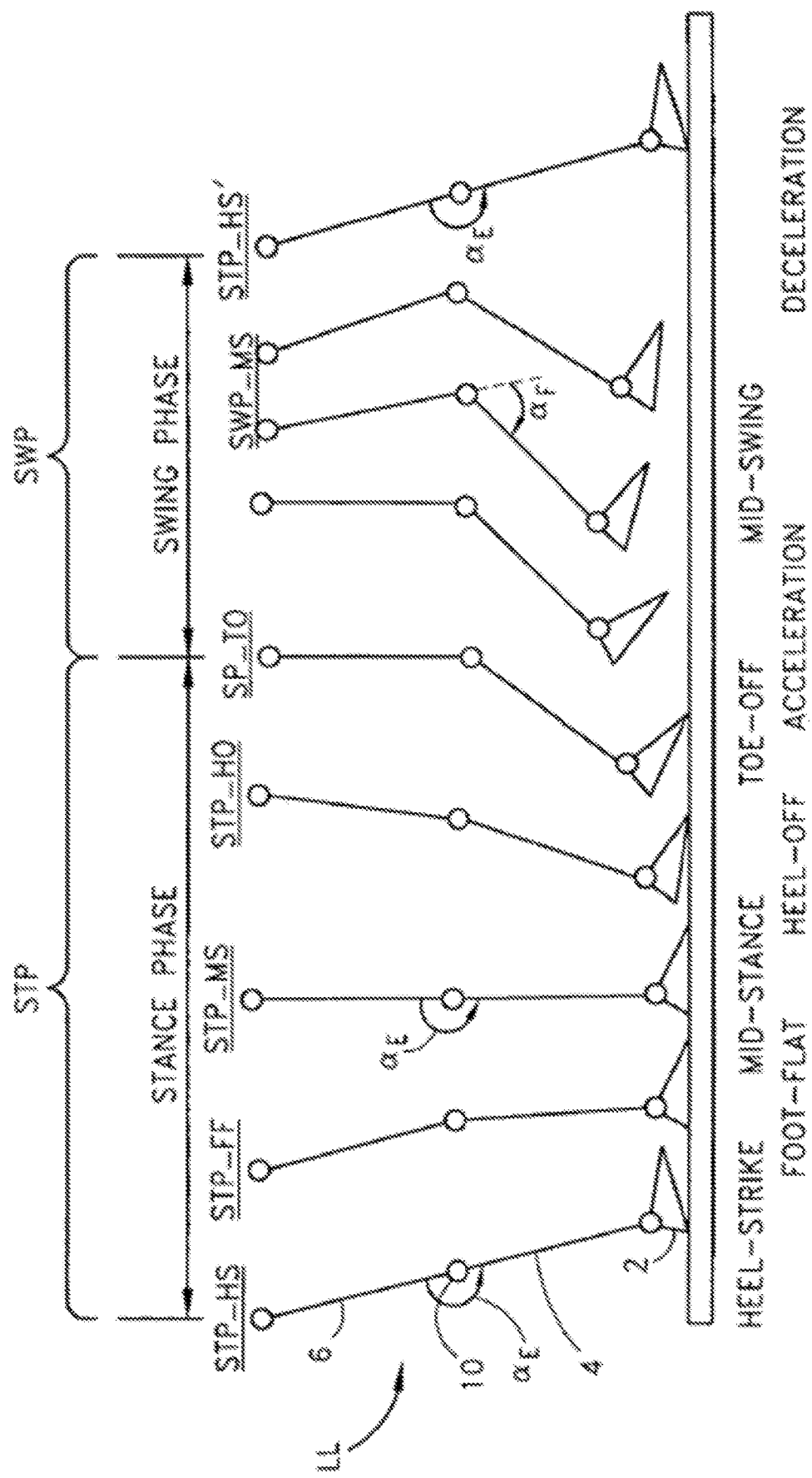
FIG. 1 is a schematic view of one normal human locomotion cycle illustrating the various limb positions during stance and swing phases.

One typical gait cycle, as schematically depicted in FIG. 1, comprises of the activity that occurs between heel strike of one lower limb LL and the subsequent heel strike of the same limb LL. The limb or leg LL generally comprises a foot 2 and a shin portion 4 coupled or articulated to a thigh portion 6 via a knee or knee joint 10. During a single gait cycle each lower limb or extremity passes through one stance or extended phase STP and one swing phase SWP.

The stance phase STP begins at heel-strike STP_HS when the heel touches the floor or supporting ground surface and the stance knee begins to flex slightly. This flexion allows for shock absorption upon impact and also maintains the body's center of gravity at a more constant vertical level during stance.

Shortly after heel-strike STP_HS, the sole makes contact with the ground at the beginning of the foot-flat phase STP FF. After maximum flexion is reached in the stance knee, the joint begins to extend again, until maximum extension is reached at mid-stance STP_MS as the body weight is swung directly over the supporting extremity and continues to rotate over the foot.

As the body mass above the ankle continues to rotate forward, the heel lifts off the ground at heel-off STP_HO. Shortly after this, the body is propelled forward by the forceful action of the calf-muscles (push-off). The push-off phase terminates when the entire foot rises from the ground at toe-off SP_TO.

During late stance, the knee of the supporting leg flexes in preparation for the foot leaving the ground for swing. This is typically referred to in the literature as "knee break". At this time, the adjacent foot strikes the ground and the body is in "double support mode", that is, both the legs are supporting the body weight.

At toe-off SP_TO, as the hip is flexed and the knee reaches a certain angle at knee break, the foot leaves the ground and the knee continues to flex into the swing phase. During early swing the foot accelerates. After reaching maximum flexion at mid-swing SWP_MS, the knee begins to extend and the foot decelerates. After the knee has reached full extension, the foot once again is placed on the ground at heel-strike STP_HS' and the next walking cycle begins.

Typically, the anatomical position is the upright position, therefore flexion is a movement of a body part away from the extended or stance or anatomical position. Thus, bending of the knee is knee flexion. Extension is a movement of a limb towards the anatomical position, thus knee extension is a movement in the "straightening" direction.

During a typical normal walking progression on a generally level surface, the maximum flexion angle $\alpha F$ varies between about 50° and 80°. The maximum extension angle $\alpha E$ is typically about or close to 180°. Thus, in level walking the normal human knee rotates through a range of approximately 50°-80° going from a position of full extension in early and mid-stance to 50°-80° of flexion shortly after toe-off. In other situations, such as, in a sitting position, the maximum flexion angle $\alpha F$ can be greater than about 50°-80° and up to, for example, about 140°-150°.

Figure 2:
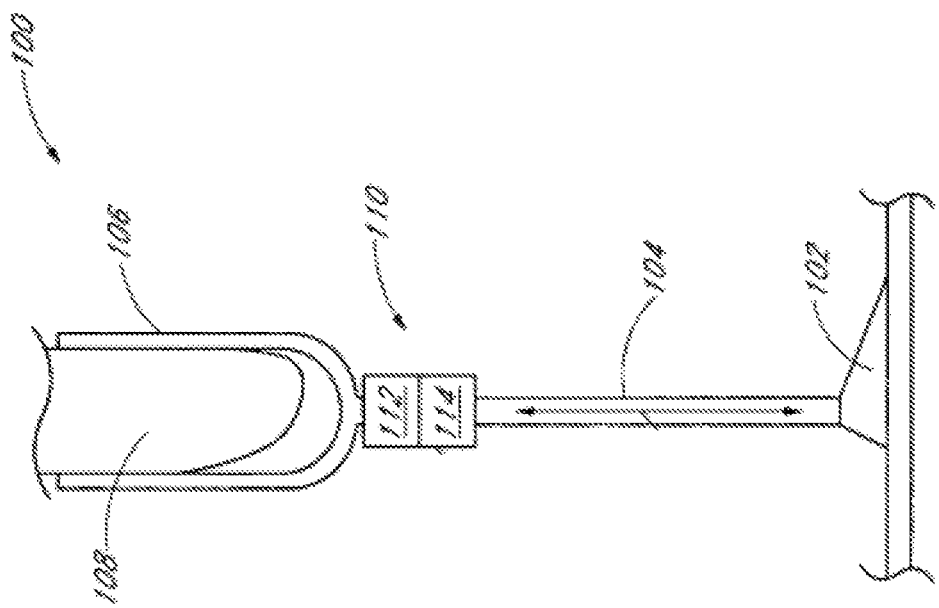
FIG. 2 is a schematic illustration of a lower limb prosthetic assembly, system or prosthesis.

FIG. 2 is a schematic illustration of a lower limb prosthetic assembly, system or prosthesis 100 including an electronically controlled active knee prosthetic assembly, system or prosthesis 110. As described in greater detail later herein, advantageously, the knee prosthesis 110 provides resistive forces to substantially simulate the position and motion of a natural knee joint during ambulation and/or other locomotory or stationary activities performed by an amputee. The prosthetic or artificial knee 110 is desirably safe, reliable and generally comfortable to use by the amputee.

The prosthetic lower limb 100 further includes an artificial or prosthetic foot 102 coupled or mechanically connected to a pylon, tube, shaft or shank portion 104 that connects to a distal or bottom portion of the prosthetic knee 110 and a residual limb or stump socket 106 that connects to a top or proximal end of the prosthetic knee 110. The stump socket 106 receives a residual limb or femur portion 108 of the amputee. A suitable pylon or the like can also be provided between the stump socket 106 and the prosthetic knee 110, as needed or desired. In some embodiments, the prosthetic knee 110 can be coupled to the user by osseointegration.

Embodiments of the disclosure can be practiced with a wide variety of prosthetic feet. These include Pro-Flex® Pivot, Pro-Flex®LP Align, Pro-Flex®LP Torsion, PROPRIO FOOT®, Pro-Flex®XC Torsion, Pro-Flex®LP, Pro-Flex®XC, Balance™Foot S Torsion, Balance™Foot S, Vari-Flex® Junior, LP Vari-Flex®, Vari-Flex®, Vari-Flex®Modular, Talux®, Re-Flex Shock™, Re-Flex Rotate™, Balance™ Foot J, Flex-Foot® Junior, Flex-Foot Balance® with D/P Flexion™, Flex-Foot Assure®, Flex-Foot Balance®, K2 Sensation®, and K2 Sensation® with D/P Flexion™.

The prosthetic knee 110 includes a variable-torque magnetorheological (MR) actuator assembly or braking system 112 and a frame and electronics assembly or system 114 that also serves as a mount for the knee actuator 112 and facilitates in monitoring and controlling the operation of the knee actuator 112. The prosthetic knee system 110 advantageously provides resistive forces to substantially simulate the position and motion of a natural knee joint during ambulation and/or other locomotory activities performed by the amputee.

Advantageously, the prosthetic knee 110 permits the amputee to move and/or adapt comfortably and safely in a wide variety of circumstances. For example, during walking, running, sitting down, or when encountering subtle or drastic changes in the terrain, topography and environment or ambient conditions, such as, when the user lifts a suitcase or walks down a slope or encounters stairs, among others.

The prosthetic knee 110 provides stance control to limit buckling when weight is applied to the limb. In addition, the prosthetic knee 110 provides aerial swing control so that the knee reaches full extension just prior to or at heel-strike in a smooth and natural manner. Moreover, the prosthetic knee 110, by adjusting and/or fine tuning the range and/or magnitudes of the resistive torque level, can be adapted for use with a wide variety of patients having different body weights, heights and activity levels.

In some implementations, the prosthetic knee assembly 110 has particular efficacy when used in conjunction with a trans-femoral (above-knee, A/N) amputee. In modified embodiments, the prosthetic knee joint 110 may be efficaciously adapted for use with a knee-disarticulation (K/D) amputee wherein the amputation is through the knee joint, as needed or desired.

In some embodiments, the variable-torque magnetorheological (MR) actuator assembly or braking system 112 can contain a magnetorheological (MR) fluid. The MR fluid is a field responsive (FR) fluid or medium that undergoes a rheology or viscosity change which is dependent on the magnitude of the applied magnetic field. In turn, this variation in fluid viscosity determines the magnitude of the shearing force/stress, torque or torsional resistance generated, and hence the level of damping provided by the knee actuator 112 and/or the prosthetic knee 110. The resistive braking effect is a function of the MR fluid viscosity which in turn is a function of the magnetic field. Thus, by controlling the magnitude of this magnetic field, the rotary motion of the artificial limb is controlled, for example, to control the flexion and extension during swing and stance phases to provide a more natural and safe ambulation for the amputee.

The MR fluid generally comprises polarizable particles, a carrier fluid, and optionally an additive. In some embodiments, as described further below, the MR fluid is specifically designed for use in a shear mode device, such as the prosthetic knee 110. For such a device, mechanically hard particles are desired. The carrier fluid also desirably experiences a less dramatic viscosity change over temperature changes as compared to other fluids.

In some embodiments, the MR fluid has one or more of the following properties: a high magnetic flux capacity and low magnetic remanence and low viscosity while having a large magnetic field induced shearing stress. Advantageously, this allows the prosthetic knee 110 to provide a wide dynamic torque range.

Figure 3:
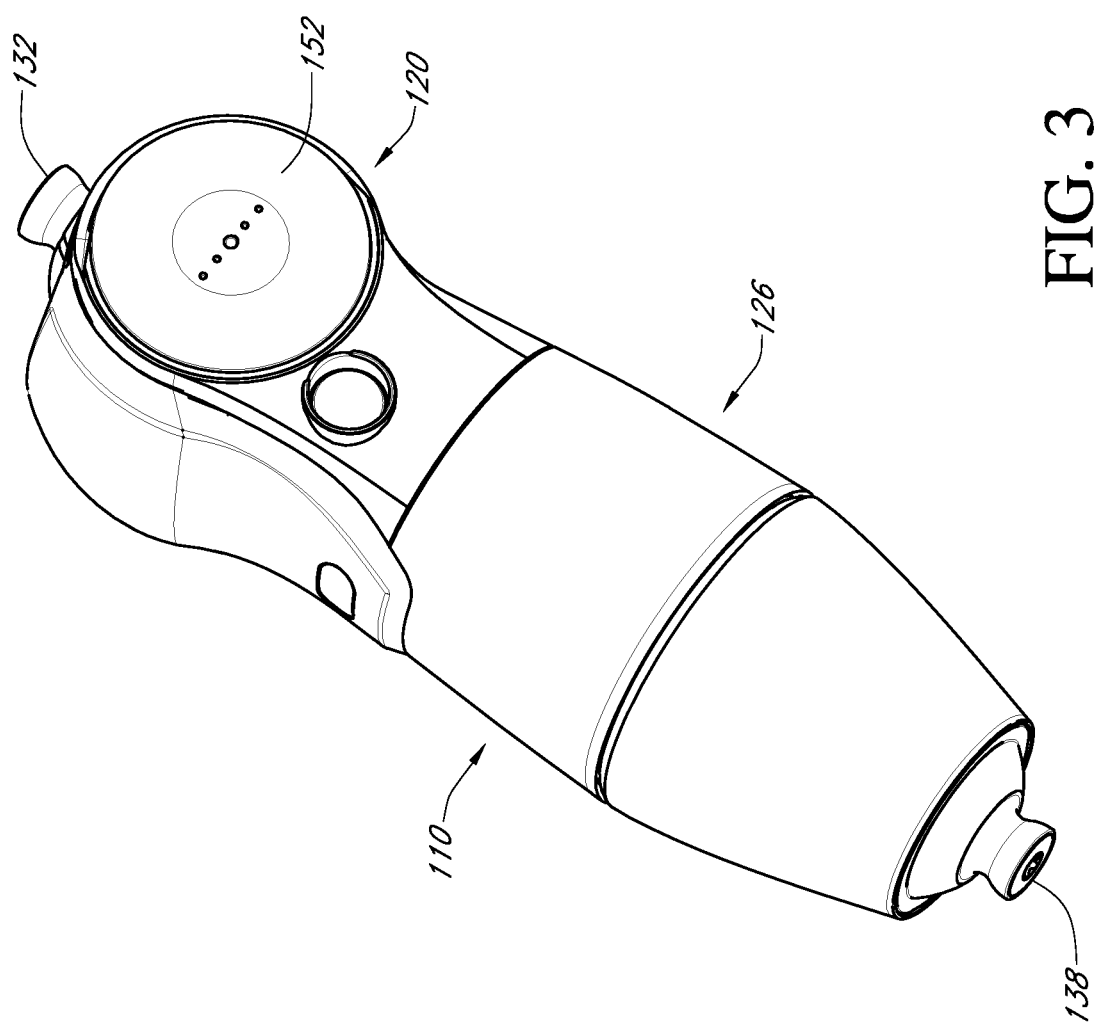
FIG. 3 is a perspective view of a prosthetic knee.

FIG. 3. depicts an embodiment of the prosthetic knee 110. The internal components of the knee 110 are inside the upper enclosure 120 and the lower enclosure 126. For example, in some embodiments the knee actuator 112 may be at least partially (e.g., completely) inside the upper enclosure 120 and the electronic assembly 114 may be at least partially (e.g., completely) inside the lower enclosure. In other embodiments, both the electronic assembly 114 and knee actuator 110 may be inside the upper enclosure 120. In the depicted embodiment, the top pyramid connector 132 can protrude from the upper enclosure 120. The bottom pyramid connector 138 can protrude from the lower enclosure 126.

Figure 4:
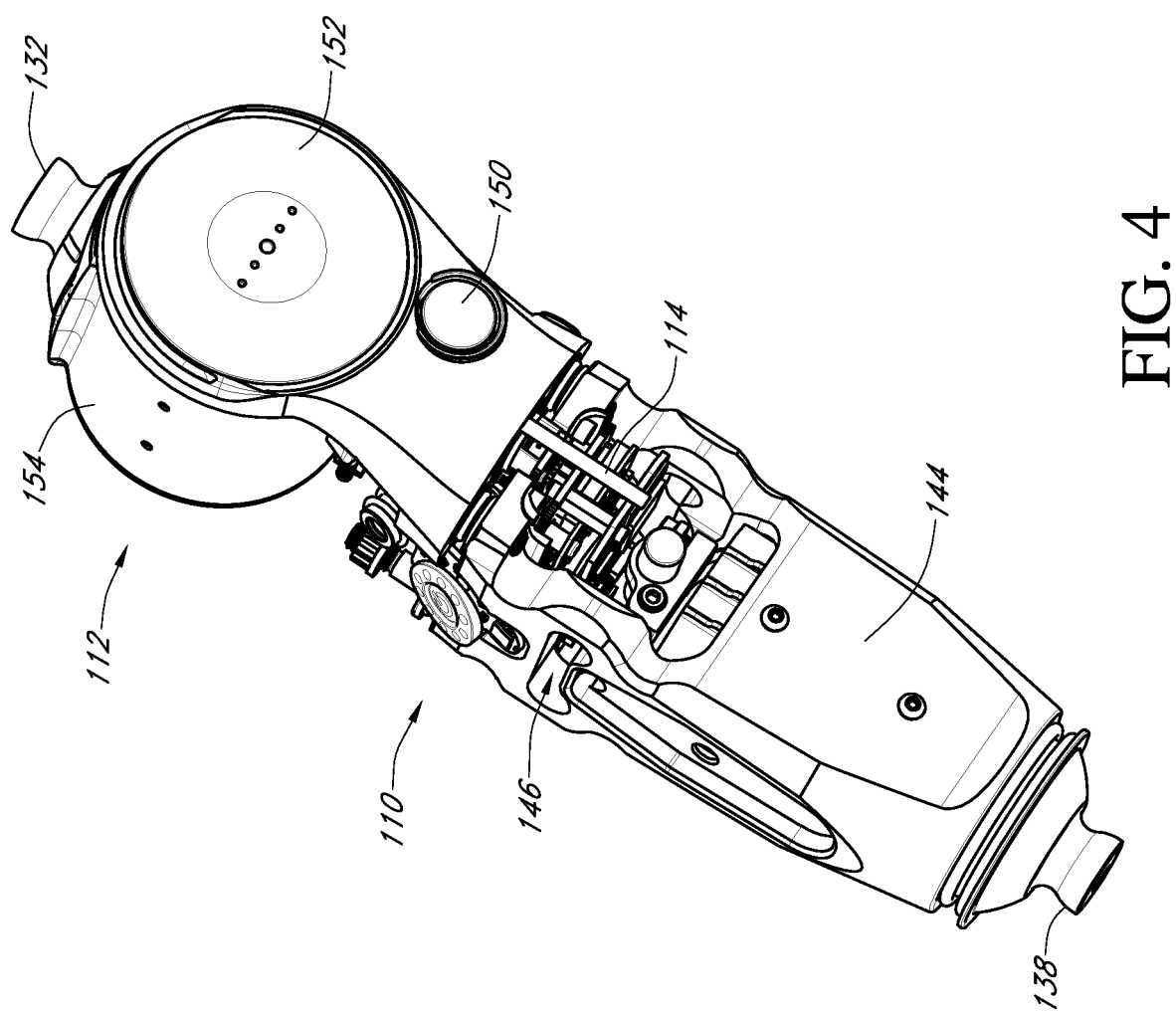
FIG. 4 is a perspective view of the prosthetic knee of FIG. 3, with a distal cover portion removed.

FIG. 4. depicts the prosthetic knee 110 with the upper enclosure 120 and the lower enclosure 126 not shown. The prosthetic knee assembly 110 includes the magnetorheological actuator assembly or system 112, the frame 144 and electronics assembly or system 114 (e.g., where the electronics 114 can be housed in the frame 144). The frame 144 maintains a rigid shape to protect the electronic assembly 114 and to enable knee 110 usage. The frame 144 can also contain a load cell 146. The electronics assembly 114 provides power and communicates with the actuator assembly 112 via electrical signals. The shown embodiment further depicts a position lock control 150 operable by a user. The position lock control 150 can be toggled to lock the knee actuator 110 in one or more positions, as further described below. In some embodiments, the position lock control 150 is toggled by sliding the position lock control 150 from side-to-side (e.g., in a medial-lateral direction). In some embodiments, a user can determine the locked status of the position lock control 150 by visual inspection (e.g., of the position of the lock control 150).

The knee actuator 112 includes a pair of side mounts 152 (only one shown), walls or forks that are mechanically coupled, communicated or connected to a core component and rotate with the core component about the knee joint axis of rotation. The side mounts 152 in combination with the outer spline 154 can form one main outer shell of the knee actuator 112. In some embodiments the outer spline 154 and the side mounts 152 form at least part of (e.g. all of) the upper enclosure 120. The side mounts 152 are connected to the frame 144 and electronics assembly 114, which in turn is connected to a lower (below the knee) part of the leg. Thus, rotation of the side mounts 152 corresponds to rotation of the lower part of the leg. The knee actuator 112 permits relative rotation between the side mounts 152 and the outer spline 154. The outer spline 154 is generally fixed relative to the upper leg of the user. The side mounts 152 are generally fixed relative to the lower leg of the user (e.g., in one implementation the side mounts 152 do not rotate relative to the rest of the prosthetic knee 110, but include a bearing that allows rotation of the knee actuator 112 that extends between the side mounts 152).

FIGS. 17-20 depicts a prosthetic knee 110A. Some of the features of the prosthetic knee 110A are similar to features of the prosthetic knee 110 in FIG. 3. Thus, reference numerals used to designate the various features or components of the prosthetic knee 110A are identical to those used for identifying the corresponding features of components of the prosthetic knee 110 in FIG. 3 except that an "A" has been added to the numerical identifier. Therefore, the structure and description for the various features of prosthetic knee 110 and how it's operated in FIG. 3 are understood to also apply to the corresponding features of prosthetic knee 110A in FIG. 20 except as described below.

Prosthetic knee 110A differs from prosthetic knee 110 in that the top pyramid connector 132A and the bottom pyramid connector 138A are multi-faceted pyramid connectors, while top pyramid connector 132 and the bottom pyramid connector 138 are round pyramid connectors.

Figure 20:
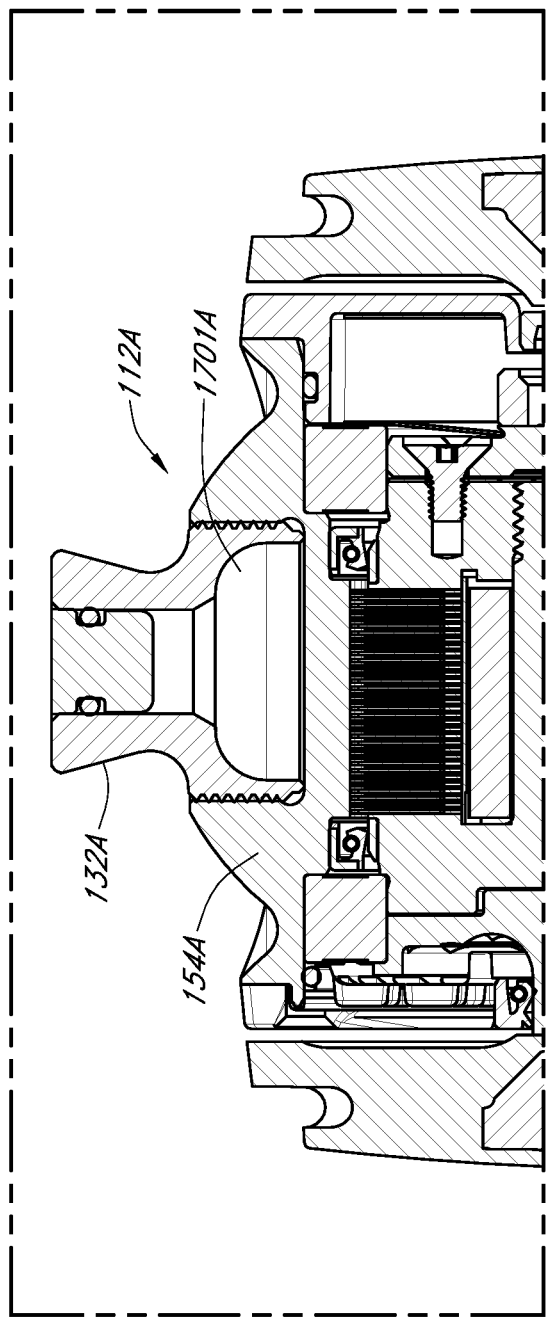
FIG. 20 is cross-sectional view of an upper portion of the prosthetic knee of FIG. 17, showing a pyramid connector.

Additionally, as shown in FIG. 20, the top pyramid connector 132A is mounted directly to an outer spline 154A. The knee actuator 112A also includes a dome 1701A integrated into the outer spline 154A.

A. Inner Blade Coupling

Figure 5:
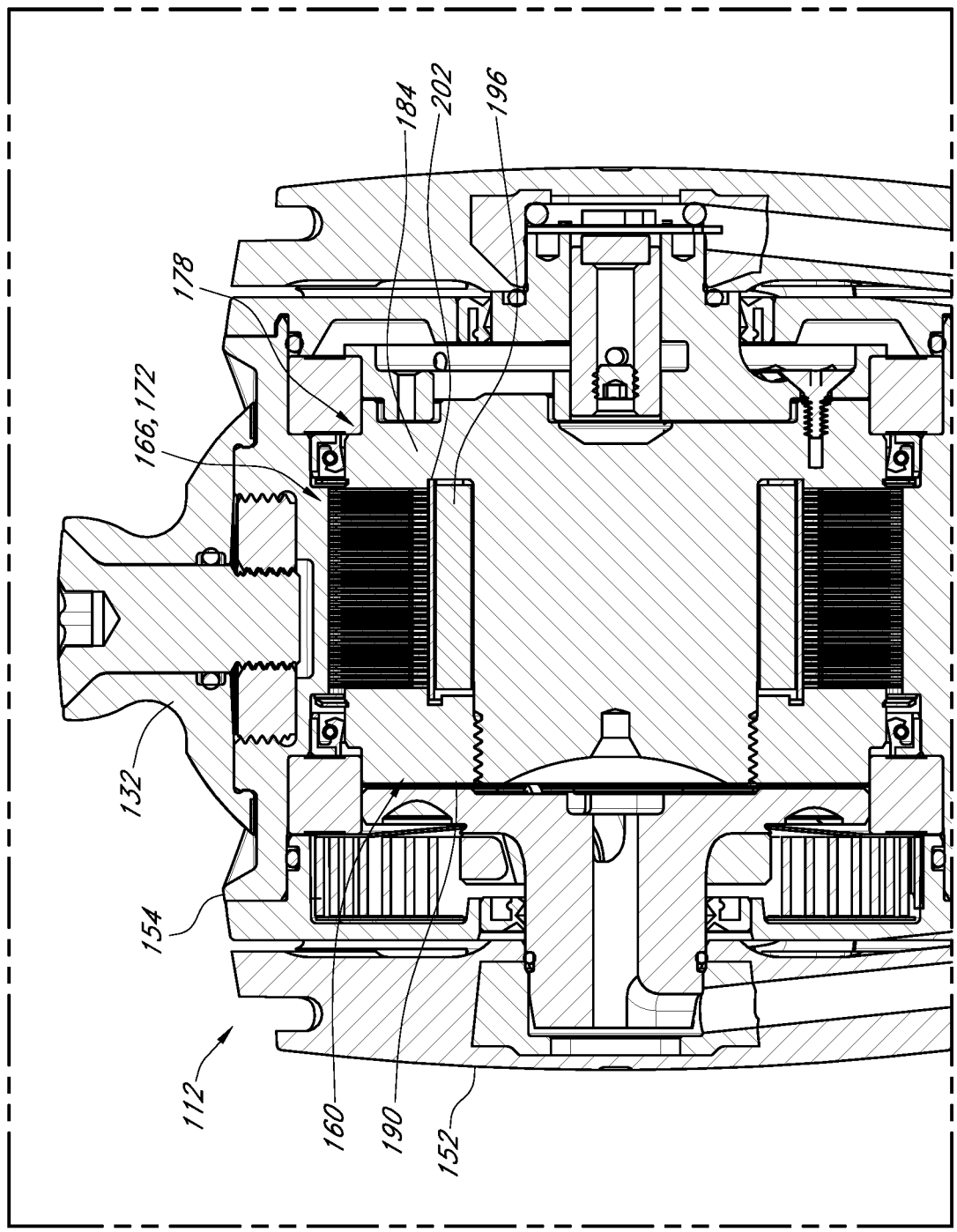
FIG. 5 is a cross-sectional view of a magnetorheological actuator of the prosthetic knee of FIG. 3.
Figure 6:
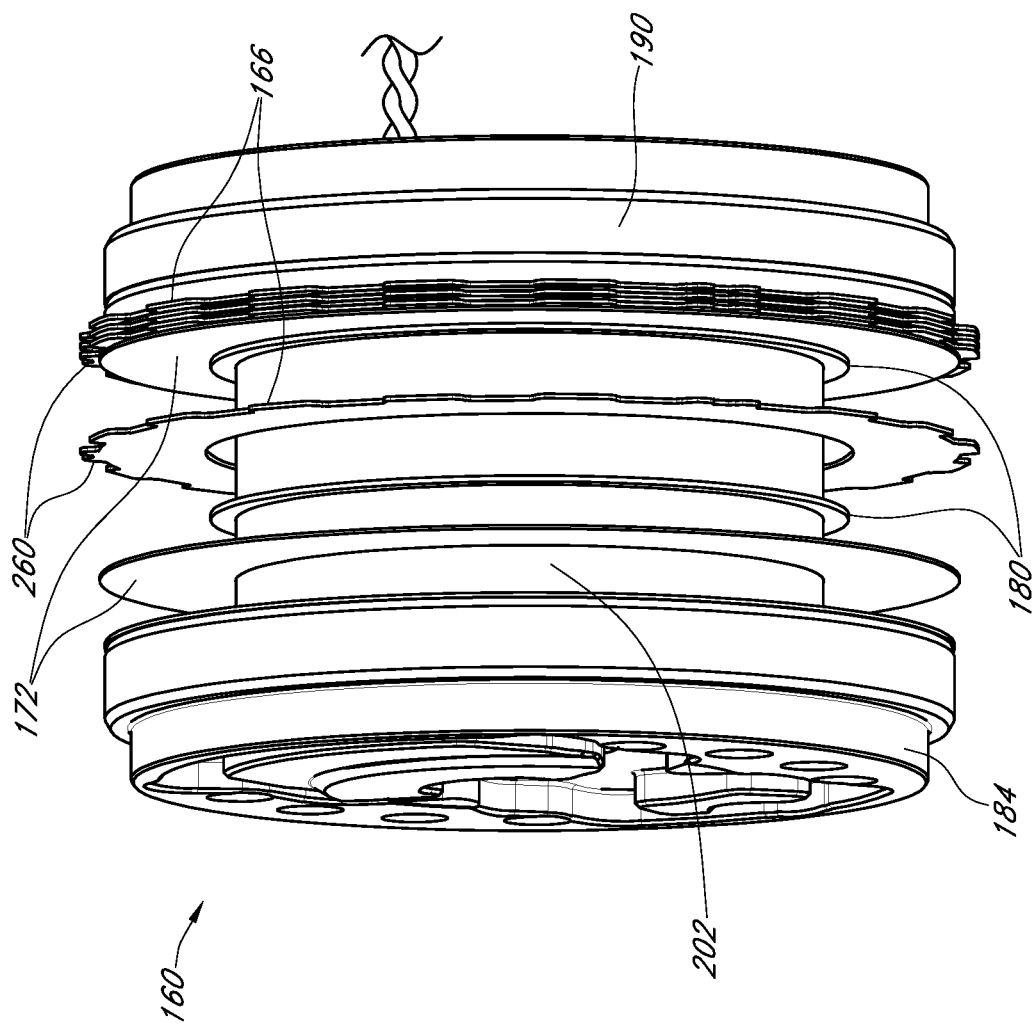
FIG. 6 is a perspective view of a blade assembly of a magnetorheological actuator for the prosthetic knee of FIG. 3.
Figure 7:
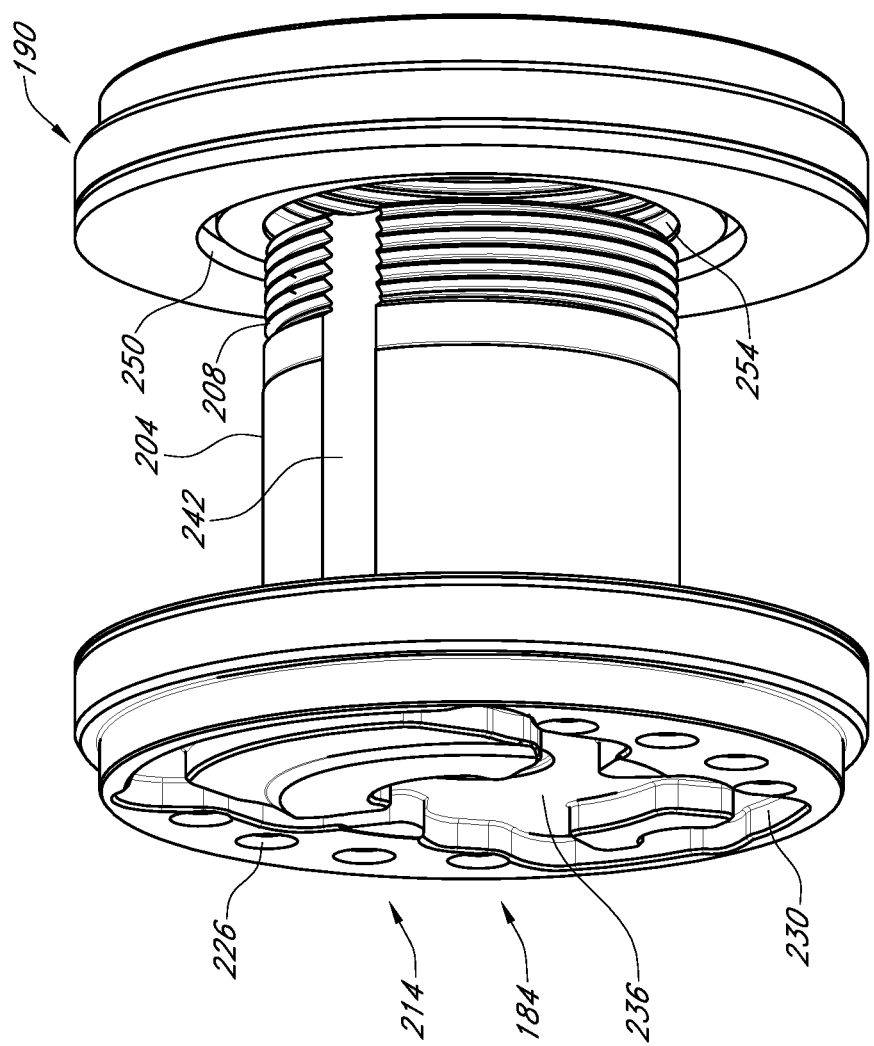
FIG. 7 is an exploded view of a screw and nut component of a core of a magnetorheological actuator for the prosthetic knee of FIG. 3.

FIG. 5 depicts a cross-sectional view of the knee actuator 112. The knee actuator 112 can have an outer spline 154. The outer spline 154 can be coupled (e.g., rigidly connected, fixedly coupled) to the top pyramid connector 132. The side mount 152 can be movably coupled to the outer spline 154. Upon movement of the knee actuator 112 (e.g., in a flexion or extension direction of the knee 110), the side mount 152 can rotate relative to the outer spline 154. The side mount 152 can be fixedly coupled to the bottom pyramid connector 138 (e.g., via the frame 144). A blade assembly 160 can be an apparatus that allows relative rotation of side mount 152 to the outer spline 154. The blade assembly 160 is shown enlarged in FIG. 6. The blade assembly 160 can have outer blades 166 coupled to the outer spline 154 and inner blades 172 coupled to the core 178. The blade assembly 160 can include spacers 180. The spacers 180 can be positioned to maintain appropriate spacing between the blades 166 and 172. Upon flexion and extension of the knee joint the inner blades 172 and outer blades 166 rotate relative to each other. A magnetorheological (MR) fluid is utilized to create an adjustable shear force between these blades in response to a magnetic field, thereby adjusting the amount of torque required to move (rotate) the knee actuator 112 (e.g. in a flexion or extension direction of the knee 110). Following user action, the knee joint will be free swinging or provided various amounts of resistance to knee motion in order to support user activity. The MR fluid fills the spaces between the blades 166 and 172.

n some embodiments, the core 178, depicted in FIGS. 5, 6, and 7 can have a screw component 184, a nut component 190 (e.g., second plate), an electromagnet coil 196, and a sheath or collar 202. The screw component 184 can have a shank 204 with a distal threaded portion 208. The threaded portion 208 can be located opposite the proximal head portion 214 (e.g., first plate). The threads can be disposed on an outer surface of the shank 204. The head portion 214 can include surface features. In some embodiments, the surface features include various holes 226. The holes 226 can be blind holes. The surface features can include cutout portions 230 that can aid in coupling the head 214 to the side mounts 152. The head 214 can include a bore hole 236. The bore hole 236 may continue into the shank 204. The bore hole 236 may continue into the threaded portion 208. The bore hole 236 can pass fully through the screw 184. The longitudinal axis of the bore hole 236 can be the longitudinal axis of the screw component 184. In some embodiments the screw 184 can have a channel 242 (e.g., linear channel) on an outer surface of the shank 204. The channel 242 can be sized and shaped to accommodate a wire 248. The wire 248 can form part of, and supply power to, the electromagnet coil 196, as further described below.

The threaded portion 208 can correspond to a threaded portion 254 on the nut component 190. In an assembled state, the screw component 184 is tightened into the nut component 190. The threads 254 on the nut are on an interior diameter. The face of the nut can have features similar to those described with respect to the head 214. The nut 190 can be fixedly coupled to the side mount 152.

The core 178 can further include the electromagnet coil 196. The coil 196 can have an inner diameter corresponding to the outer diameter of the shank 204, so that the coil 196 can be positioned about the shank 204. The coil 196 can be arranged such that the wire 248 is positioned within the channel 242. A sheath 202 can be positioned about (e.g., surrounding) the coil 196. The sheath 202 can have a length that generally corresponds to the length of the shank 204. The sheath 202 is useful to protect the coil 196. Ends of the sheath 202 can be retained in grooves 250 in the head 214 and nut 190 (e.g., so that the sheath 202 extends coaxially with the shank 204 and coil 196.

FIG. 6 shows the assembled blade assembly 160. In this view various blades 166 and 172 are not shown for clarity purposes. In some embodiments, the knee actuator 112 can include 65 blades (e.g., 33 outer blades 166 coupled to the outer spline 154 and 32 inner blades 172 coupled to the core 178). However, other suitable number of blades can be used in the knee actuator 112 based on specification requirements of the actuator 112. The blades can be arranged such that the blades alternate between inner blade 172 and outer blade 166. In some embodiments, the outermost blade on both the screw 184 side and nut 190 side is an outer blade 166.

The outer blades 166 are generally annular. The blades 166 can have a splined outer edge 260. The outer diameter, and the splines 260, on the outer blades 166 can be sized and shaped to correspond to an inner splined surface of the outer spline 154. The splines on the outer blades 166 and the splines on the outer spline 154 can correspond and can mate. The motion of the outer blades 166 can correspond to motion of the outer spline 154. The motion of the outer blades 166 and the outer spline 154 can be rotational motion (e.g., about the axis of the shank 204). The outer blades 166 can have an inner diameter that is greater than the outer diameter of the sheath 202. The outer blades 166 can have a thickness that is less than the thickness of the spacers 180 and the outer blades 166 can have an inner diameter that is larger than the outer diameter of the spacers 180. The outer diameter of the outer blades 166, as measured to the root of the splines is approximately equal to the outer diameter of the head portion 214.

The spacers 180 are generally annular. The spacers 180 can have a thickness greater than the thickness of the outer blades 166. The spacers 180 can have an outer diameter that is less that the inner diameter of the outer blades 166. The inner diameter of the spacers can be slightly larger than the outer diameter of the sheath 202. The spacers 180 are arranged to be clamped between adjacent inner blades 172 and advantageously inhibit play and wear due to play between the blades 172 during operation of the knee actuator 112.

The inner blades 172 are generally annular. The inner blades 172 can have a smooth outer surface. The inner diameter of the inner blades 172 can be slightly larger than the outer diameter of the sheath 202. The outer diameter of the inner blades 172 can be approximately equal to the outer diameter of the head portion 214.

In the assembled state the inner blades 172 and outer blades 166 alternate. The spacers 180 are positioned between the outer blades 166 and the sheath 202. Since the spacers 180 are thicker than the outer blades 166, the spacers 180 protrude to either side of the outer blades 166. The assembled core 178 applies an axial loading in the direction of the shank 204. This loading pushes the inner blades 172 against the spacers. In the fully assembled condition the spacers 180 and inner blades 172 and outer blades 166 are firmly clamped (e.g., compressed) between the head portion 214 and the nut 190. The desired tightness can be reached by threading threaded portion 208 into threads 254. The axial loading can be sufficient to prevent relative motion between the inner blades 172 and the core 178. Since the spacers 180 protrude to either side of the outer blades 166 there is a gap between the planar surfaces of the outer blades 166 and the inner blades 172. This gap can be filled with MR fluid. The size of this gap can be between 0.01 and 0.08 mm. The size of the gap can preferably be 0.05 mm. The thickness of the outer blades 166 and the spacers can be selected to select a thickness of the MR fluid. The thickness of the MR fluid between each pair of outer blades 166 and inner blades 172 can, in one implementation be equal to one-half of the difference between the outer blade 166 thickness and the spacer 180 thickness. The entire planar surface on both sides of the inner blades 172 are used for shearing resistance during movement of the knee actuator 112.

In some embodiments, the inner blades, outer blades can be made of hardened spring steel. The outer spline can be made from aluminum. The core can be made from vacoflux 50. The spacers can be made of a non-magnetic material. For example, the spacers can be made of titanium.

Coupling the inner blades 172 to the core 178 by friction improves the performance of the knee actuator 112 by reducing play between the inner blades 172 and the core 178. It is especially helpful in reducing play due to wear between the inner blades 172 and the core 178. The inner blades 172 can be simple annular shapes that are low cost to manufacture.

B. Lock Mechanism

Figure 8:
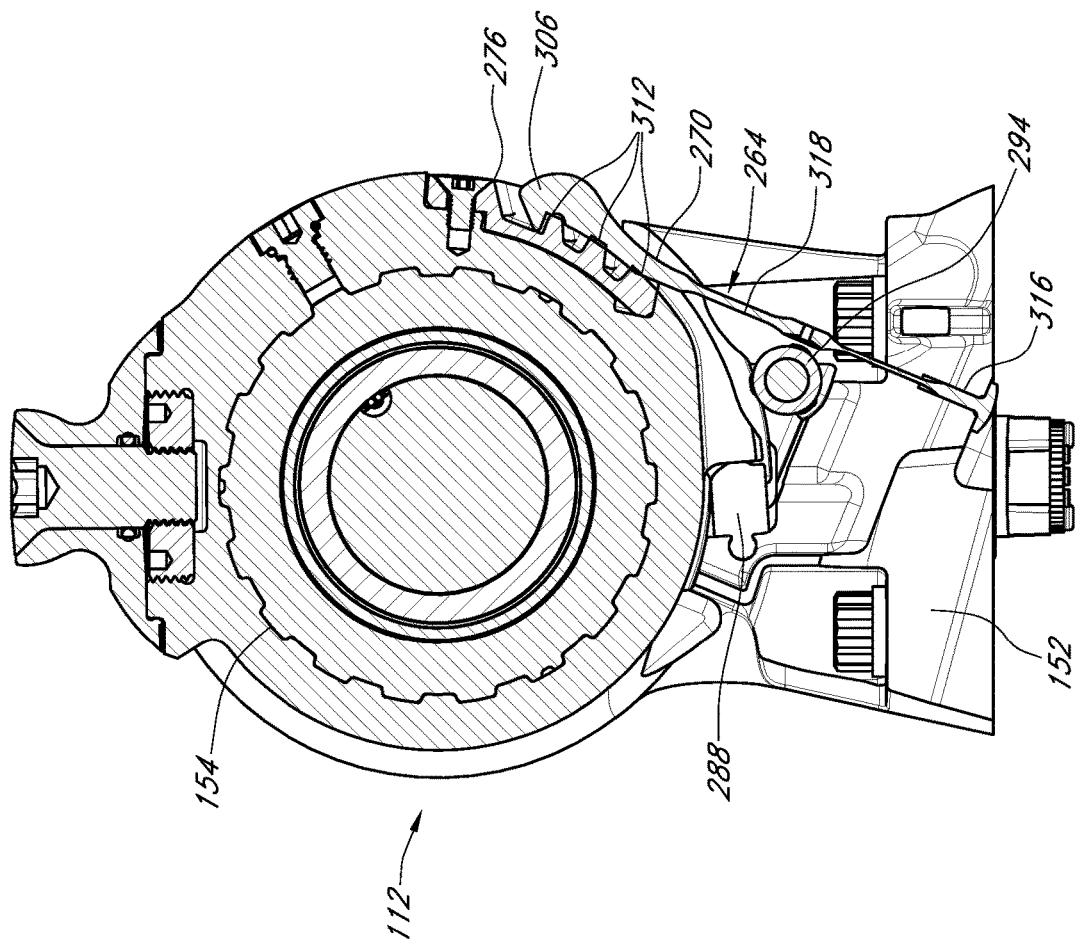
FIG. 8 is a cross-sectional view of a magnetorheological actuator of the prosthetic knee of FIG. 3.
Figure 9A:
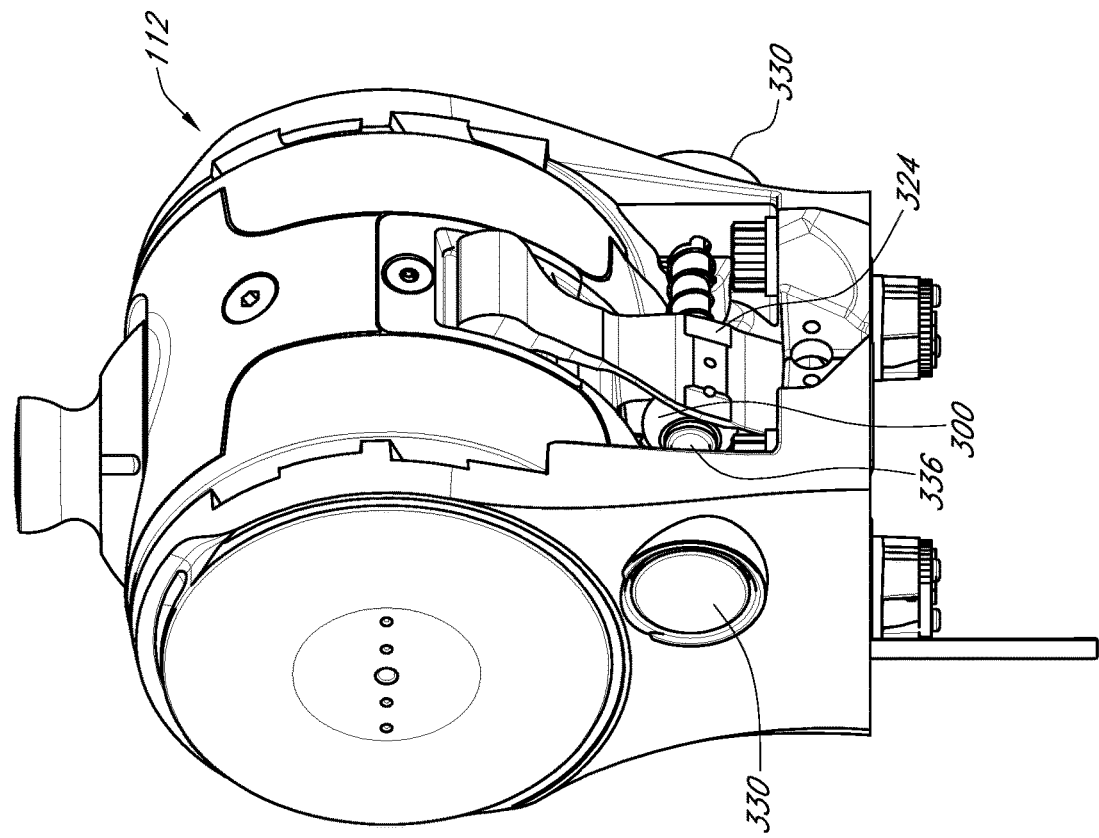
FIG. 9A is a perspective view of the actuator of the prosthetic knee of FIG. 3 depicting a locking mechanism in one operating configuration.
Figure 9B:
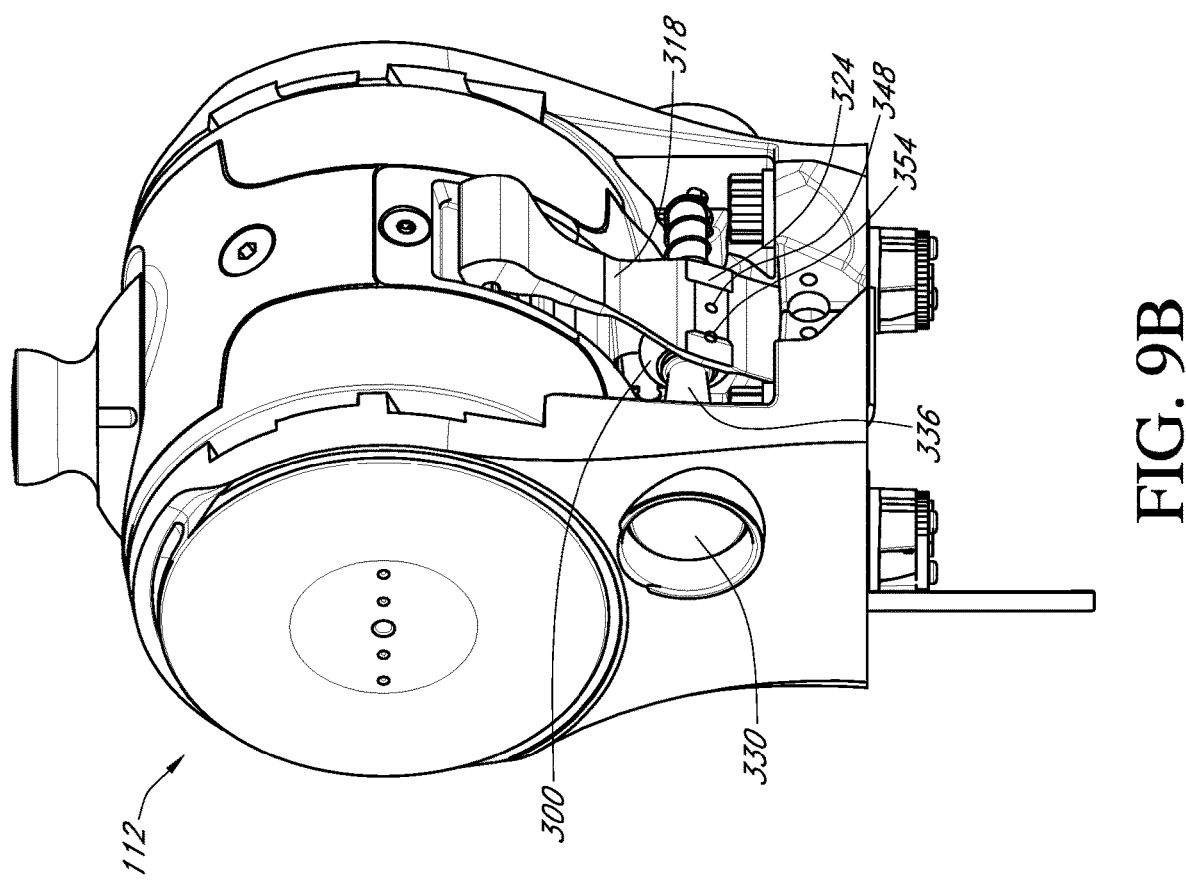
FIG. 9B is a perspective view of the actuator of the prosthetic knee of FIG. 3 depicting a locking mechanism in another operating configuration.
Figure 10:
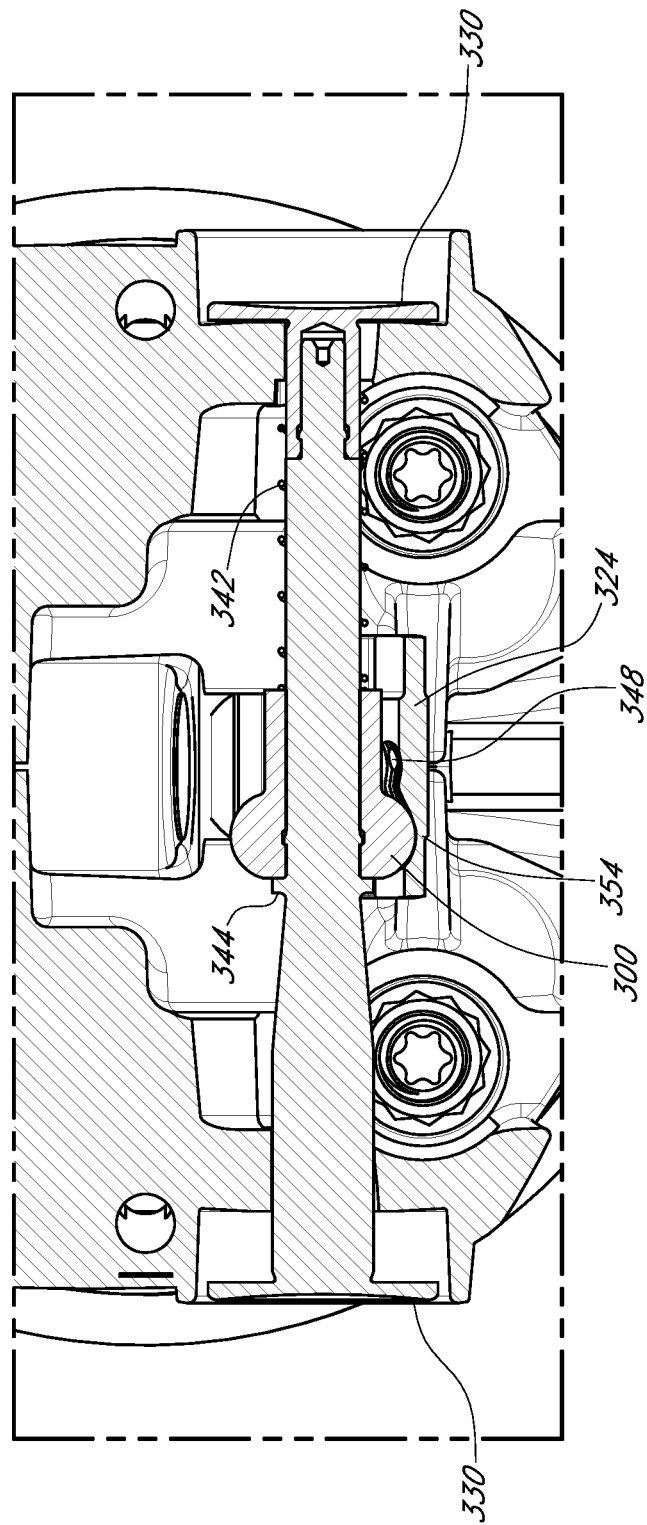
FIG. 10 is a partial cross-sectional view of a portion of a lock toggle assembly for the prosthetic knee of FIG. 3.

FIGS. 8-10 depict components of the knee actuator 112, and especially components related to a lock mechanism for the knee actuator 112. FIG. 8 depicts a cross-sectional view of knee actuator 112. The knee actuator 112 can include a position lock assembly 264. The position lock assembly 264 can lock the position of the outer spline 154 relative to the side mount 152. The position lock assembly 264 can lock the degree of rotation of the knee 110. In some embodiments, the position lock assembly 264 can allow ratcheting in the extension direction and prevent motion in flexion direction. In some embodiments, the position lock assembly 264 can be activated and deactivated (e.g., manually) by a user.

The position lock assembly 264 can have a blade 270. The blade 270 can have a hook or engagement member sized and shaped to releasably engage one or more teeth of a toothed profile 276 on the outer spline 154. When the blade 270 is engaged with one or more teeth of the toothed profile 276, flexion motion of the knee actuator 112 is inhibited (e.g., prevented). When the blade 270 is disengaged from the one or more teeth of the toothed profile 276, flexion motion of the knee actuator 112 is uninhibited (e.g., allowed). The blade 270 can be engaged or disengaged with the toothed profile 276 based on a position of a lock toggle assembly 294. The lock toggle assembly 294 can be coupled to the blade 270 via a lock member 300. The lock member 300 can in one implementation be a ball or ball-shaped. In other implementations, the lock member 300 may instead be a wheel, cylindrical, spheroidal, or have another suitable shape. The knee actuator 112 may also have an extension stop bumper 288 that limits the maximum extension of the knee actuator 112. At maximum extension, rotation of the knee actuator 112 is restricted by the extension stop bumper 288. The stop bumper 288 may restrict further extension in excess of a maximum extension. The stop bumper 288 can be fixed to the side mount 152. The stop bumper 288 can bear against the outer spline 154 to restrict the movement of the outer spline 154 relative to the side mount 152. The outer spline 154 can have a ledge or shoulder feature for bearing against the stop bumper 288.

In some embodiments, when the lock toggle assembly 294 is engaged, rotation of the knee actuator 112 is restricted by the mating of toothed profile 276 and blade 270 (e.g., hook of blade 270). The mating of toothed profile 276 and blade 270 may restrict (e.g., prevent) further flexion of the knee actuator 112. The mating of toothed profile 276 and blade 270 may permit movement of the knee actuator 112 in the extension direction (e.g., until limited by the extension stop bumper 288). The toothed profile 276 can be fixed to the outer spline 154. The blade 270 can be movably coupled with the side mount 152. The coupling of blade 270 to the side mount 152 can facilitate bearing of the blade 270 on the side mount 152 when the toothed profile 276 mates with the blade 270. In the depicted embodiment, the blade 270 is fixed (e.g., cantilevered) onto the side mounts 152, and the blade 270 flexes when the lock member 300 acts on the blade 270.

In the depicted embodiment, the lock toggle assembly 294 is mounted on an anterior side of the knee actuator 112. In some embodiments, the lock toggle assembly 294 could be mounted on a posterior side.

The blade 270 can have a hook 306. The hook 306 can be sized and shaped to engage with the one or more teeth 312 of the toothed profile 276. The hook 306 can have a ramp or tapered shape on a first side, and the ramp shape can slide on a ramp portion of a tooth 312. Opposite the ramp, the hook 306 can have a grip portion. The grip portion can be flat or another shape and can prevent motion relative to a mating surface of a tooth 312. The teeth 312 can apply a force to the ramp of the hook 306. This force can tend to push the locking blade hook 306 away from the toothed profile 276. In some embodiments, the locking blade 270 can deflect way from the toothed profile when loaded. In some embodiments, the locking blade 270 can deflect enough to allow the hook 306 to disengage from the toothed profile, thereby allowing the outer spline 154 to rotate relative to the side mounts 154. The locking blade 270 can have a bending portion 318. The bending portion 318 can preferentially bend under various loading conditions. The bending portion 314 can be a narrowed portion of the locking blade 270. The blade 270 can be generally elongate with the hook 306 at a distal end thereof. A connector 316 can be affixed to the blade 270 at a proximal end (e.g., at the opposite end of the blade 270 from the hook 206), the connector 316 coupling the locking blade 270 to the side mount 252. The bending portion 318 can be located along the length of the blade 270 and in between the distal and proximal ends. In some embodiments, the bending feature can be the entire locking blade 270, or any portion thereof.

The toothed profile 276 can have one or more teeth 312. For example, and as shown in the depicted embodiment, the toothed profile 276 can have 3 teeth. However, in other implementations, the toothed profile 276 can have fewer or more teeth. The teeth correspond to degrees of flexion of the knee joint. As described above, the teeth 312 can have with a ramp portion and a flat portion. The ramp may be suitable for sliding relative to the locking blade 270 in a first direction (e.g., counterclockwise motion of the outer spline 154 in FIG. 8). The flat portion may be suitable for locking relative to the locking blade 270 in a second direction (e.g., clockwise motion of the outer spline 154 in FIG. 8). The toothed profile 276 can be fixedly coupled to the outer spline 154.

FIG. 9A depicts a portion of a prosthetic knee in a locked configuration. FIG. 9B depicts a portion of a prosthetic knee in an unlocked configuration. In the depicted embodiment, the toothed profile 276 and locking 270 are engaged when the position lock assembly 264 is in a first configuration and are disengaged when the position lock assembly 264 is in a second configuration.

When the lock assembly 264 is engaged, locking blade 270 hooks on tooth profile 276 thereby restricting rotation of outer spline 154 in flexion direction. Ratcheting in the extension direction is possible due to the flexibility of locking blade 270 in combination with the shape of the tooth profile 276 and the shape of the locking blade hook 306. At maximum extension, rotation is restricted by the extension bumpers 288. When the lock assembly 264 is disengaged, rotation of the knee actuator 112 is not restricted by the blade 270. Disengaging the lock assembly can position the locking blade 270 such that it does not contact the tooth profile 276 (e.g., space the tooth 306 of the blade 270 apart from the toothed profile 276 so that the blade 270 clears the toothed profile 276 as the knee actuator 112 is rotated).

Lock toggle assembly 294 is actuated to engage/disengage the blade 270 from the toothed profile 276 by the movement of the lock member 300 into a desired position. When the lock toggle assembly 294 is actuated to disengage the blade 270 from the toothed profile 276 (e.g., unlock the knee actuator 112), such as by sliding the lock toggle assembly 294 in one direction, the lock member 300 is positioned (e.g., in a shallower hole of a collar or slider in which the lock member 300 travels) to push the locking blade 270 outwards (e.g., away from the toothed profile 276). The locking blade 270 clears the toothed profile 276 when it is in the disengaged configuration. When the lock toggle assembly 294 is actuated to engage the blade 270 from the toothed profile 276 (e.g., lock the knee actuator 112), such as by sliding the lock toggle assembly 294 in an opposite direction, the lock member 300 is moved to the side (e.g., in a deeper hole of a collar or slider in which the lock member 300 travels), allowing the blade 270 (e.g., hook 306 of the blade 270) to contact the toothed profile 276 and to snap into a locking position. The blade 270 can be deflected outward when the lock assembly 294 is actuated to disengage the position lock assembly 264. The outward deflection of blade 270 can store energy in the blade 270. The energy can be stored in a bending portion 318. The energy can be released to move the blade 270 back into an engaged position. In some embodiments, the lock member 300 is held in a locked/unlocked position by the shape of a blade slider 324. In some embodiments, the locking blade 270 exerts a force on the lock member 300. The force can tend to hold the lock member 300 in a locked/unlocked position. The blade slider 324 can be located between the proximal and distal ends of the blade 270. The blade slider 324 can be located between the connector 316 and the hook 306 of the blade 270. The lock toggle assembly 294 can have two minimum energy positions. The minimum energy positions corresponding to the engaged/disengaged status of the position lock assembly 264. The blade 270 and slider 324 can have two minimum energy positions, one for each of locked/unlocked positions. The minimum energy positions are such that the lock member 300 tends to fall to one of the two minimum energy positions. The blade 270 and slider 324 cooperate such that the lock member 300 tends to assume one of the two positions, each position corresponding to an engaged/disengaged state of the lock assembly 264. Advantageously, the two minimum energy positions allows that position lock assembly 264 to either move to a lock or unlocked position for the knee actuator 112 (e.g., via engagement of the hook 306 of the blade 270 with the toothed profile 276) even when the lock toggle assembly 294 is not actuated (e.g., moved, slid) into a position between the two minimum energy positions.

In some embodiments, the position lock assembly 264 can be engaged/disengaged by translation of the lock toggle buttons 330. The toggle buttons 330 can be affixed on the two ends of a shaft 336 and can be accessible through apertures disposed on the side mounts 152. The shaft 336 can span the knee actuator 112. Disposed on the shaft 336 can be the lock member 300. The lock member 300 can be fixedly attached to the shaft 336. In some embodiments, there is a spring 342 disposed to one side of the lock member 300. The spring can be useful to prevent the lock member 300 from occupying a position that is not one of the minimum energy positions defined by the blade slider 324. The lock member 300 can contact the blade slider 324. The lock member 300 can be hollow with the shaft 336 extending through the lock member 300. The shaft 336 can have a tab feature 344. The tab feature 344 can be a circumferential ridge. The tab feature and the spring 342 can act on opposite sides of the lock member 300. The tab feature and the spring 342 can apply force to the lock member 300.

FIG. 10 depicts a portion of a prosthetic knee 110 in cross-section. In FIG. 10, the blade slider 324 is shown in cross section. The blade slider 324 can have two minimum energy positions, each minimum energy position corresponding to an engaged/disengaged configuration of the position lock assembly 264. The minimum energy positions are positions on the slider 324 where the lock member 300 can be stably positioned. A first minimum energy position could be a first indent 348 (e.g., shallower hole in the slider 324). The first indent 348 can be located along the centerline of the blade 270 (e.g., aligned with a centerline of the blade 270, see FIG. 9B). The second minimum energy position could be a second indent 354 (e.g., deeper hole in the slider 324). The second indent 354 can have a steep ramp on one side, and a shallow ramp on a second side. The second indent 354 can be located off-center to the blade 270. The second indent 354 can be deeper than the first indent. When the lock member 300 is positioned in the first indent 348, the blade 270 can be deflected outwards relative to the actuator 112 (e.g., deflected away from the knee actuator 112) to a disengaged position with the toothed profile 276 (e.g., knee actuator 112 is unlocked to motion in flexion). When the lock member 300 is positioned in the second indent 354, the blade 270 can be in an engaged position with the toothed profile 276 (e.g., the knee actuator 112 is locked to inhibit or prevent motion in flexion). In some embodiments, the first indent 348 and the second indent 354 can be through holes on the slider 324.

The second indent 354 can be deeper than the first indent 348. When the lock member 300 is in in the first indent 348, the lock member 300 can apply a force to the bladed 270 and flex the blade 270 to unlock the knee actuator 112. The lock assembly 294 can, in one implementation, have an audible click when the lock assembly 294 is engaged or disengaged to provide the user with an audible indication of the locking and/or unlocking of the knee actuator 112. A ridge can be positioned between first indent 348 and second indent 354. The ridge can be angled so as to get feedback when the lock member 300 clicks over barrier from one hole to the other.

When the blade 270 and toothed profile 276 are engaged there can be various locked positions of the knee 110. Each of the teeth 312 can correspond to a locked position for the knee 110. The different locked positions are realized based on which tooth 312 the blade 270 is locked against. For example, the various locked positions of the knee 110 could include: standing with knee straight, or knee in full flexion (such as when leaning against a wall or sitting on a high chair—such as a bar stool).

Figure 21A:
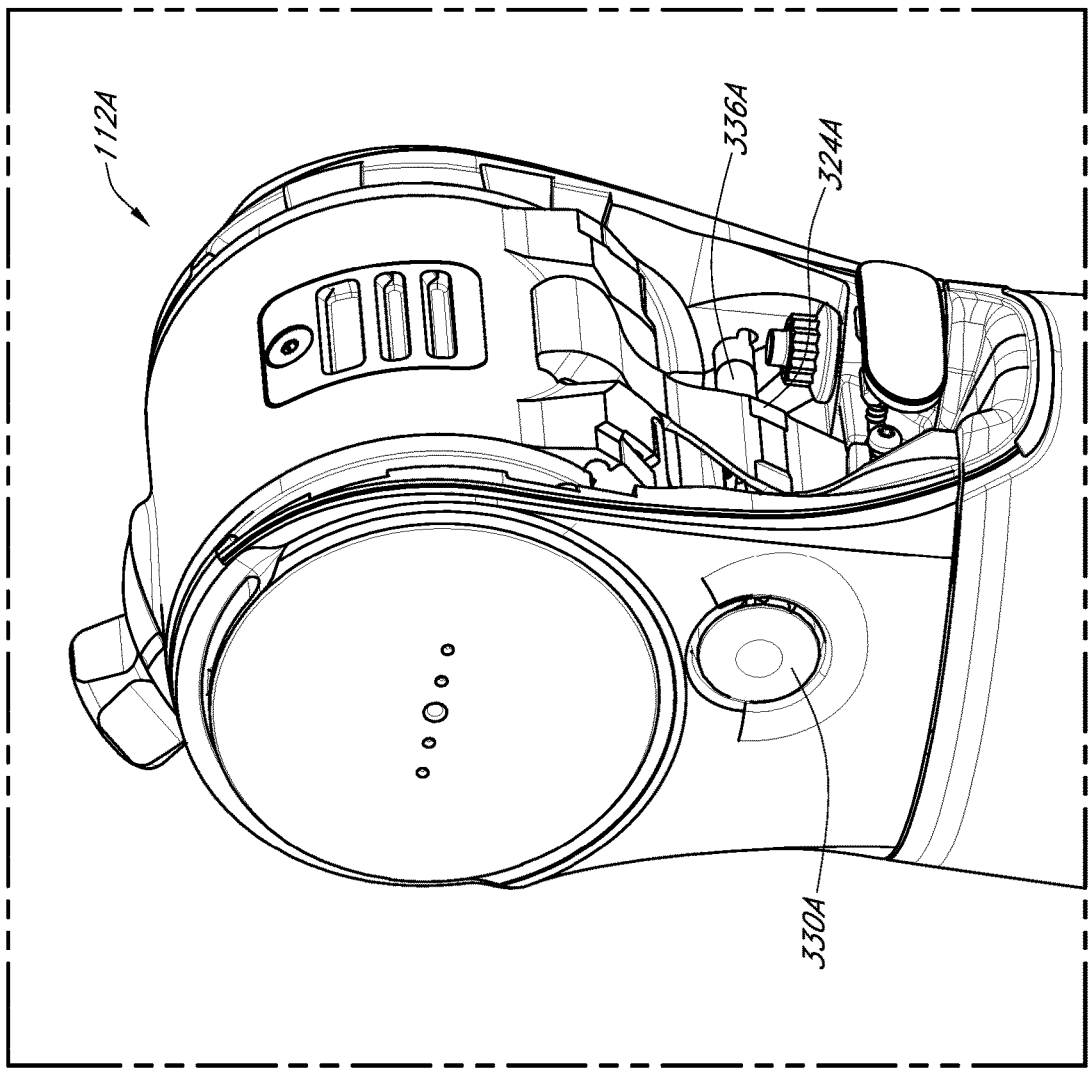
FIGS. 21A-21B are a perspective view of the upper portion of the prosthetic knee of FIG. 17 showing a locking mechanism.
Figure 21B:
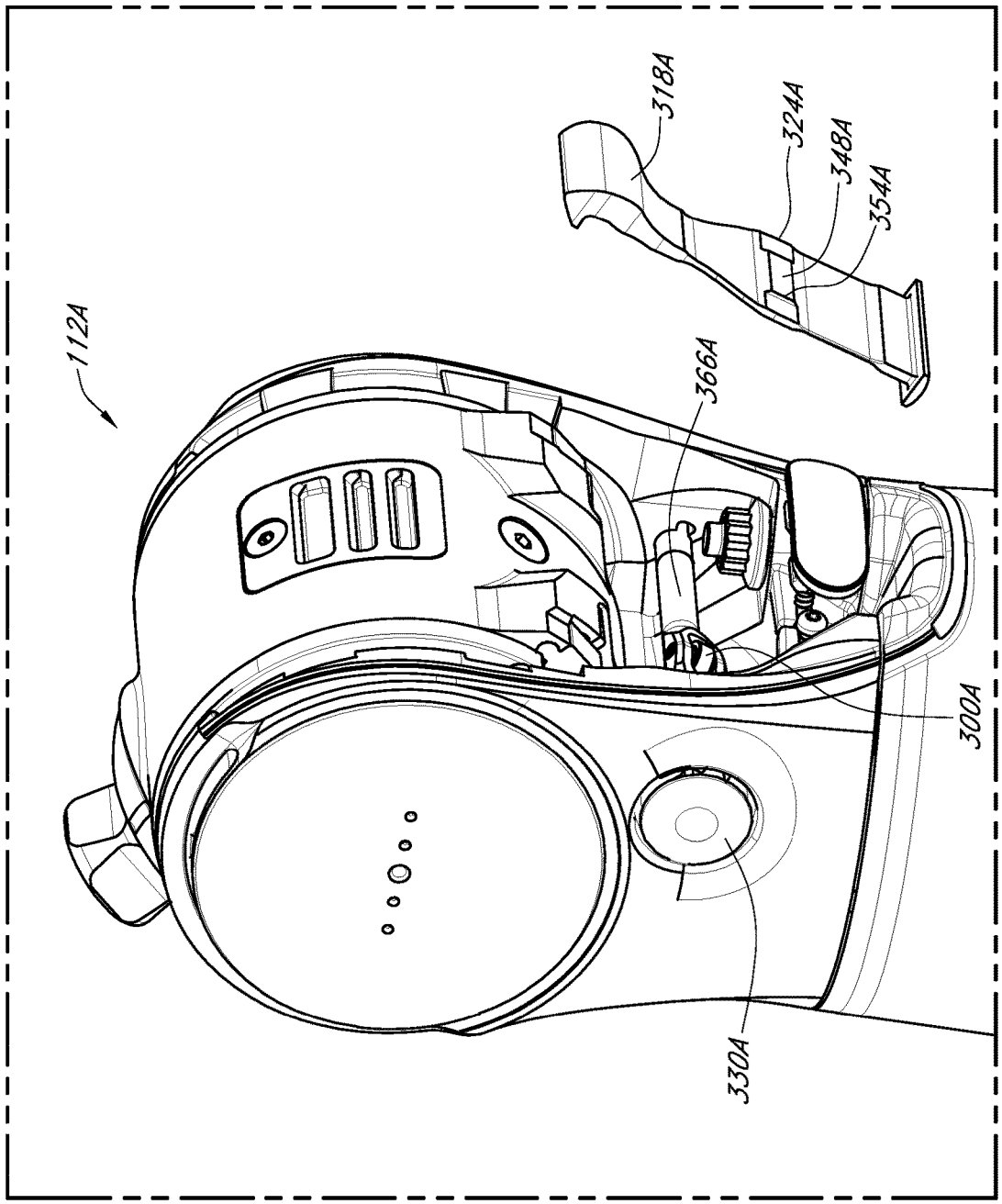
Figure 22:
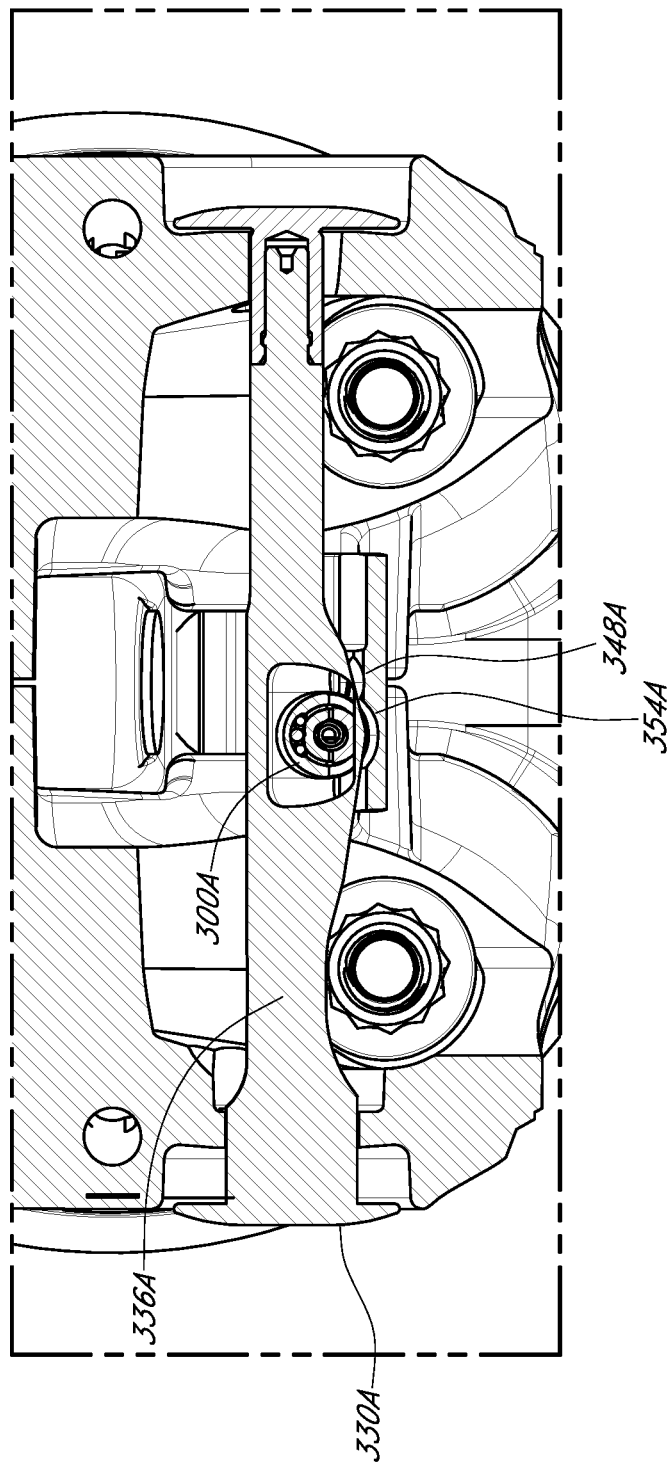
FIG. 22 is a partial cross-sectional view of a portion of a lock toggle assembly for the prosthetic knee of FIG. 17.

FIGS. 21A-21B show perspective views of an upper portion of the knee actuator 112A of the prosthetic knee 110A (shown in FIGS. 17-20), illustrating the position lock assembly 264A, lock toggle assembly 294A and blade 270A. FIG. 22 shows a cross-sectional view of a portion of the prosthetic knee 110A showing components of the position lock toggle assembly 294A. Some of the features of the position lock assembly 264A, lock toggle assembly 294A and blade 270A are similar to features of the position lock assembly 264, lock toggle assembly 294 and blade 270 in FIGS. 8-10. Thus, reference numerals used to designate the various features or components of the position lock assembly 264A, lock toggle assembly 294A and blade 270A are identical to those used for identifying the corresponding features of components of the position lock assembly 264, lock toggle assembly 294 and blade 270 in FIGS. 8-10 except that an "A" has been added to the numerical identifier. Therefore, the structure and description for the various features of the position lock assembly 264. lock toggle assembly 294 and blade 270 and how it's operated in FIGS. 8-10 understood to also apply to the corresponding features of the position lock assembly 264A, lock toggle assembly 294A and blade 270A in FIGS. 21A-22, except as described below.

The lock toggle assembly 294A differs from the lock toggle assembly 294 in that the lock member 300A is a wheel 300A rotatably coupled to the shaft 336A. Additionally, the lock toggle assembly 294A does not have a spring (e.g. similar to spring 342) disposed about the shaft 336A. The wheel 300A is sized to at least partially fit in the first indent 348A and second indent 354A during operation of the lock toggle assembly 294A to cause the position lock assembly 264A to engage or disengage from the toothed profile or teeth 276A of the knee actuator 112A.

C. Seal Protector

Figure 11:
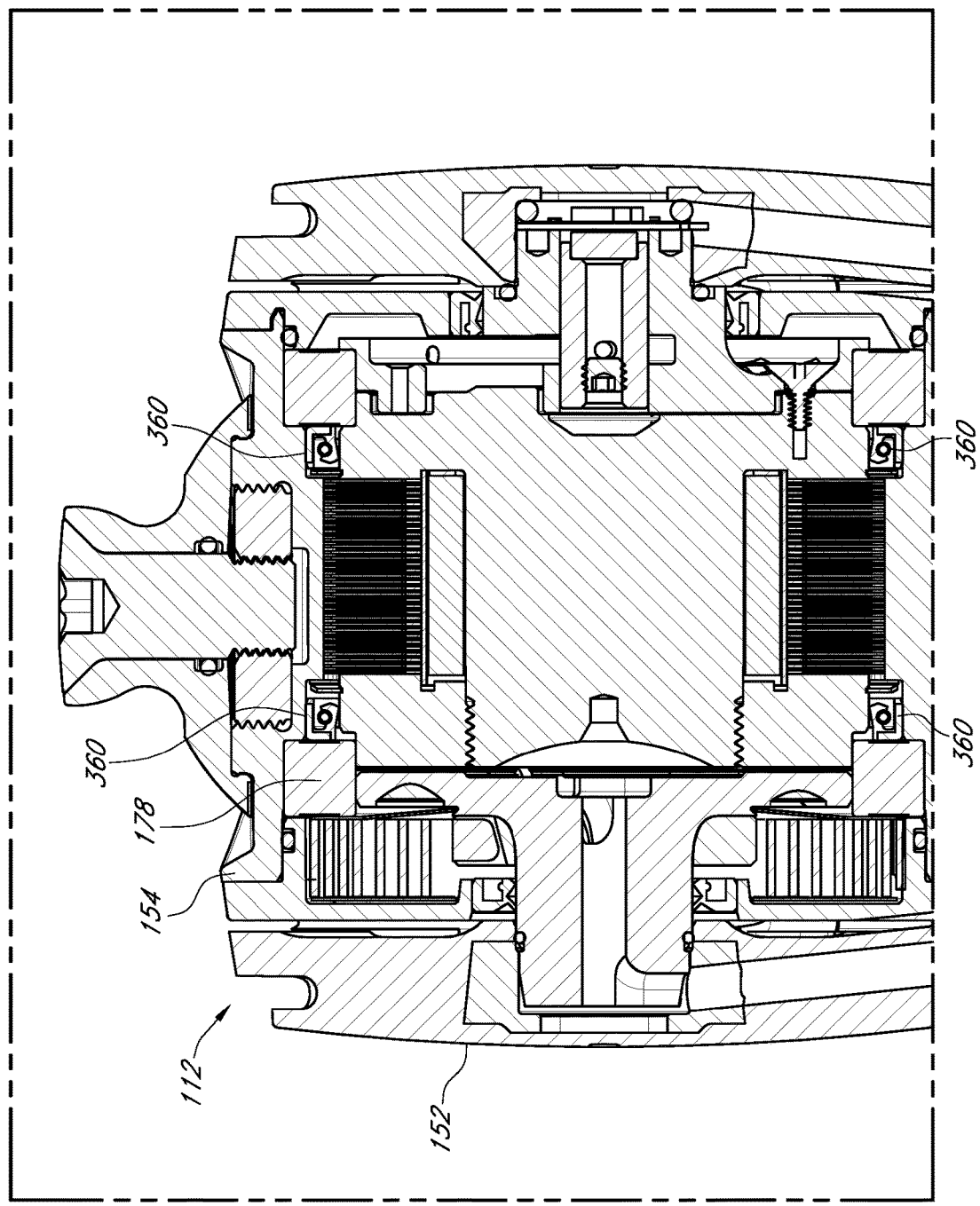
FIG. 11 is a cross-sectional view of a magnetorheological actuator for a prosthetic knee.

FIG. 11 shows a cross-section view of a knee actuator 112. The knee actuator 112 can include a dynamic seal assembly 360. The knee actuator 112 consists of a series of blades 166, 172 alternately coupled to the outer spline 154 and the core 178 of the knee actuator 112. Upon flexion and extension of the knee actuator 112, the inner and outer blades 166, 172 rotate relative to each other. A magnetorheological (MR) fluid is utilized to create an adjustable shear force between the blades 166,172 in response to a magnetic field, thereby adjusting the amount of torque required to move (rotate) the knee actuator 112 (e.g., relative to the lower portion of the prosthetic knee 110). The MR-fluid is kept inside the knee-actuator 112 via the dynamic seal assembly 360 placed between the outer spline 154 and core 178. Following user action, the knee actuator 112 will be free swinging or provided various amounts of resistance to knee motion in order to support user activity.

Figure 12:
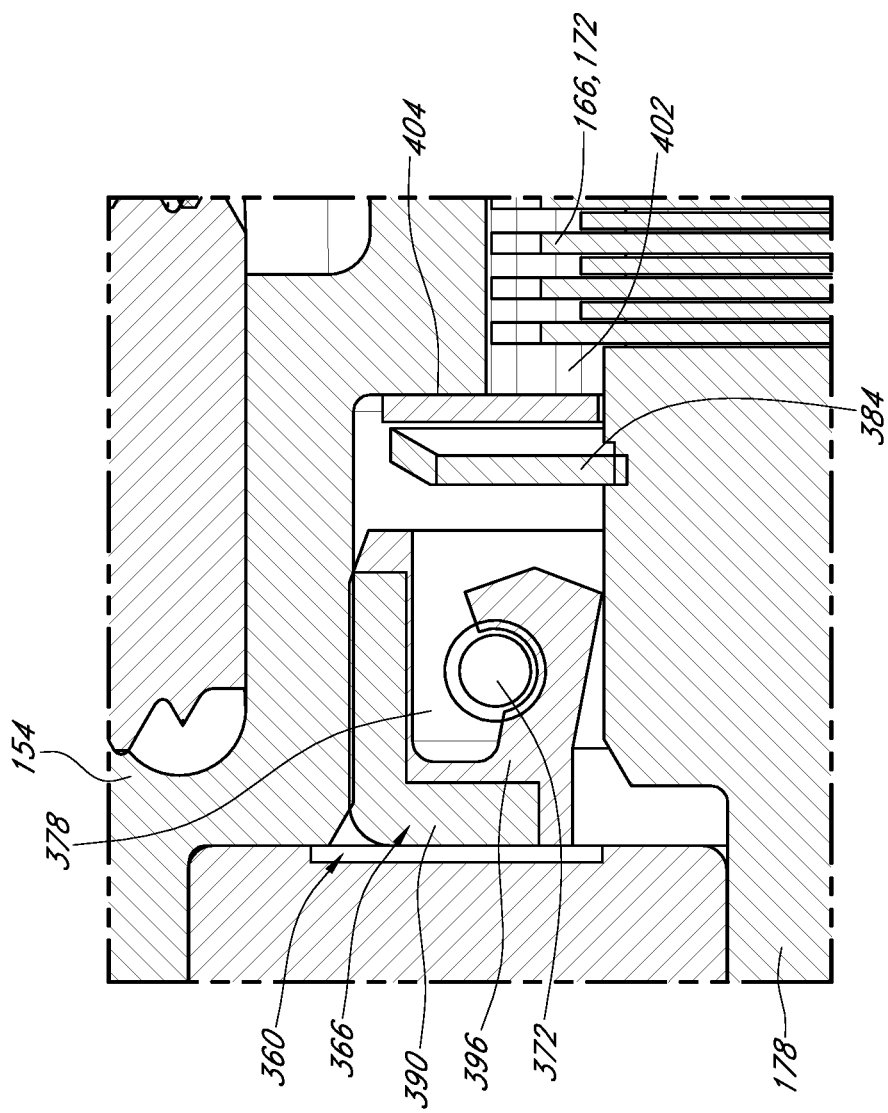
FIG. 12 is an enlarged cross-sectional view of a dynamic seal assembly of a magnetorheological actuator for a prosthetic knee.

FIG. 12 shows a close-up cross-section view of the dynamic seal assembly 360. The dynamic seal assembly 360 can include a dynamic rotary seal 366, a spring 372, the grease filled cavity 378, and a seal protector shim 384. Spring 372 can be include one or more of a seal spring, a coiled spring, a metal spring, and a polymer spring. The dynamic rotary seal 366 can be positioned between the outer spline 154 and core 178. The dynamic rotary seal 366 can have a metal ring 390 and a non-metal (e.g., polymer) portion 396. The metal ring 390 and non-metal (e.g., polymer) portion 396 can be molded as a single component. The combined metal ring 390 and non-metal (e.g., polymer) portion 396 can be annular. The dynamic rotary seal 366 can have a cavity 378 filled with grease. The cavity can include the space within the spring 372. The selected grease preferably does not react/dissolve with MR fluid and has a low shear resistance. In the illustrated embodiment, the space between the seal protector shim 384 and the cavity 378 is also filled with grease. The seal protector shim 384 can have an annular shape. The seal protector shim 384 advantageously inhibits (e.g., impedes) the migration of MR fluid 402 from around the blades 166, 172 to the dynamic seal 366, thereby inhibiting (e.g., preventing) migration of iron particles in the MR fluid from into the dynamic seal cavity and spring 372 and inhibiting (e.g., preventing) leakage of MR fluid.

The shim can 384 can be fixedly coupled to the core 178 as shown in FIG. 12. The shim 384 can have an inner diameter approximately equal to an outer diameter of the core 178. The outer diameter of the shim 384 can be less than an inner diameter of the outer spline 154. The shim 384 can be shaped to have a clearance of about 0.2 mm to 0.5 mm. The clearance is measured between the outer diameter of the shim 384 and the inner diameter of the outer spline 154. In some embodiments, the shim 384 rotates with the core. The shim 384 can be positioned circumferentially about the core 178. The shim 384 can be positioned longitudinally between the dynamic seal 366 and a portion of the outer spline 154. In some embodiments, the outer spline 154 can have a constriction or ledge 404. The constriction 404 can be a portion of the outer spline 154 where the inner diameter of the outer spline 154 changes for a first diameter to a second diameter. The shim 384 can be positioned longitudinally between the dynamic seal 366 and the constriction 404 of the outer spline 154. The shim 384 can be made of any type of flexible plastic material (e.g., nylon or polyoxymethylene. Making the shim 384 of flexible material can advantageously reduce wear if the shim 384 comes into contact with the constriction 404.

Figure 13:
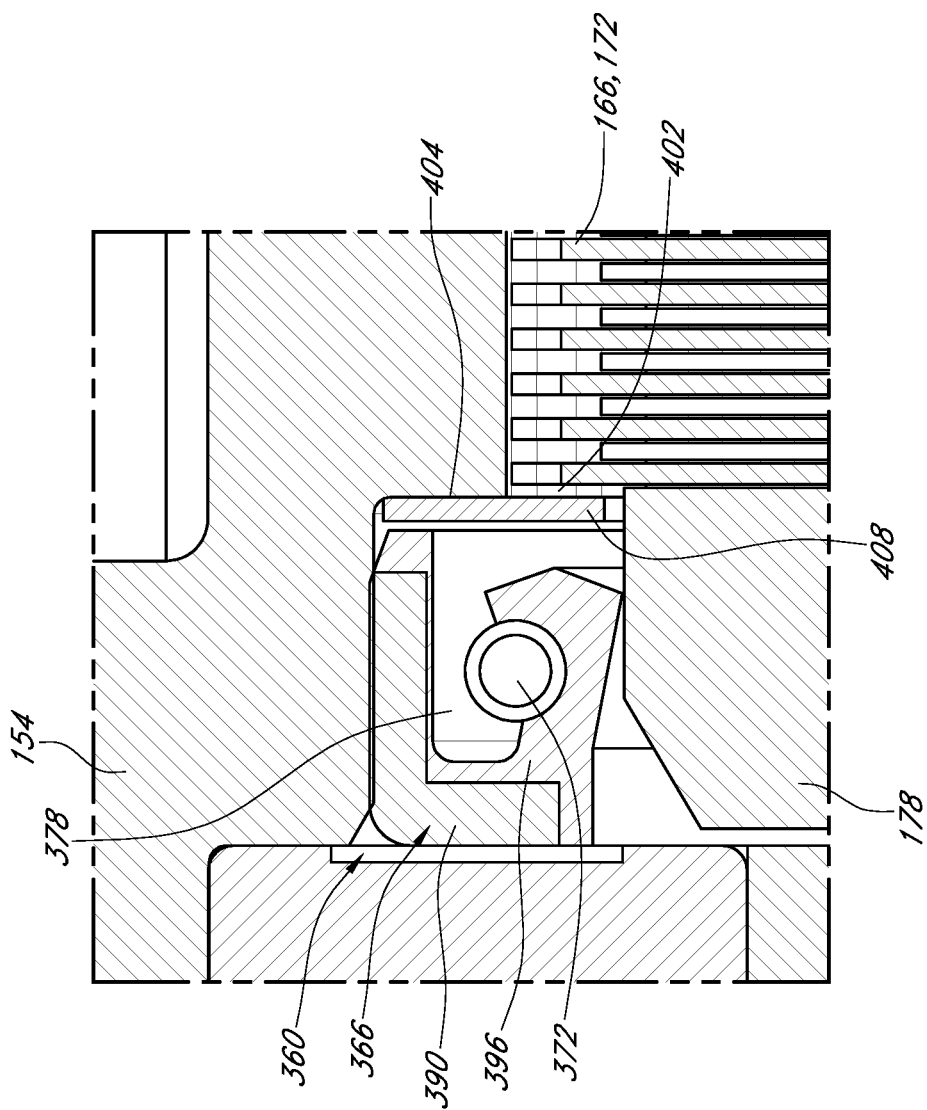
FIG. 13 is an enlarged cross-sectional view of a dynamic seal assembly of a magnetorheological actuator for a prosthetic knee.

In some embodiments, and as depicted in FIG. 13, the shim used in the dynamic seal assembly can be a movable or floating shim 408. The moveable shim 408 may be similar in many aspects to the seal protector shim 384. The movable or floating shim 408 can be movably coupled to the core 178. The movable shim 408 can have an inner diameter than is equal to or greater than the outer diameter of the core 178. The movable shim 408 can have an outer diameter that is less than an inner diameter of the outer spline 154. The movable shim 408 can translate along the core from a position proximate to the dynamic seal 366 to a position distal to the dynamic seal 366. The movable shim 408 can translate along the core from a position proximate to the constriction 404 to a position distal to the constriction 404. The movable shim 404 can be made of a nonmagnetic metal (e.g., aluminum or titanium). Advantageously, if the movable shim 404 bears against the constriction 404, it can move away from it.

The shim 384, 408 can impede iron particles from moving towards the polymer of the seal 366. The grease 378 can impede iron particles from moving towards the polymer of the seal 366. The shim 384,408 is coupled to the core 178 (movably or fixedly) and elongates the path between the MR-fluid 402 and seal 366 surface and serves as a barrier between the grease 378 and the MR-fluid 402. MR-fluid 402 does not get in contact with the dynamic seal. This advantageously leads to improved durability of the knee actuator 112 as it prevents leakage of MR-fluid 402 and prevents the iron particles from migrating out of the active MR-fluid 402.

In another implementation, the seal protector 384 is not movable and is attached (e.g., via an interference fit) to the outer spline 154. This advantageously reduces the gap between the dynamic seal assembly 360 and the seal protector 384 and achieves a more even gap with the core 178 because of the reduced concentricity error associated with a loose fit on the outer diameter of the seal protector 384. Optionally, seal protector 384 can be made of non-metallic material, for example, to facilitate interference fitting. In another implementation, the seal protector 384 can be excluded from the knee actuator 112.

Figure 19:
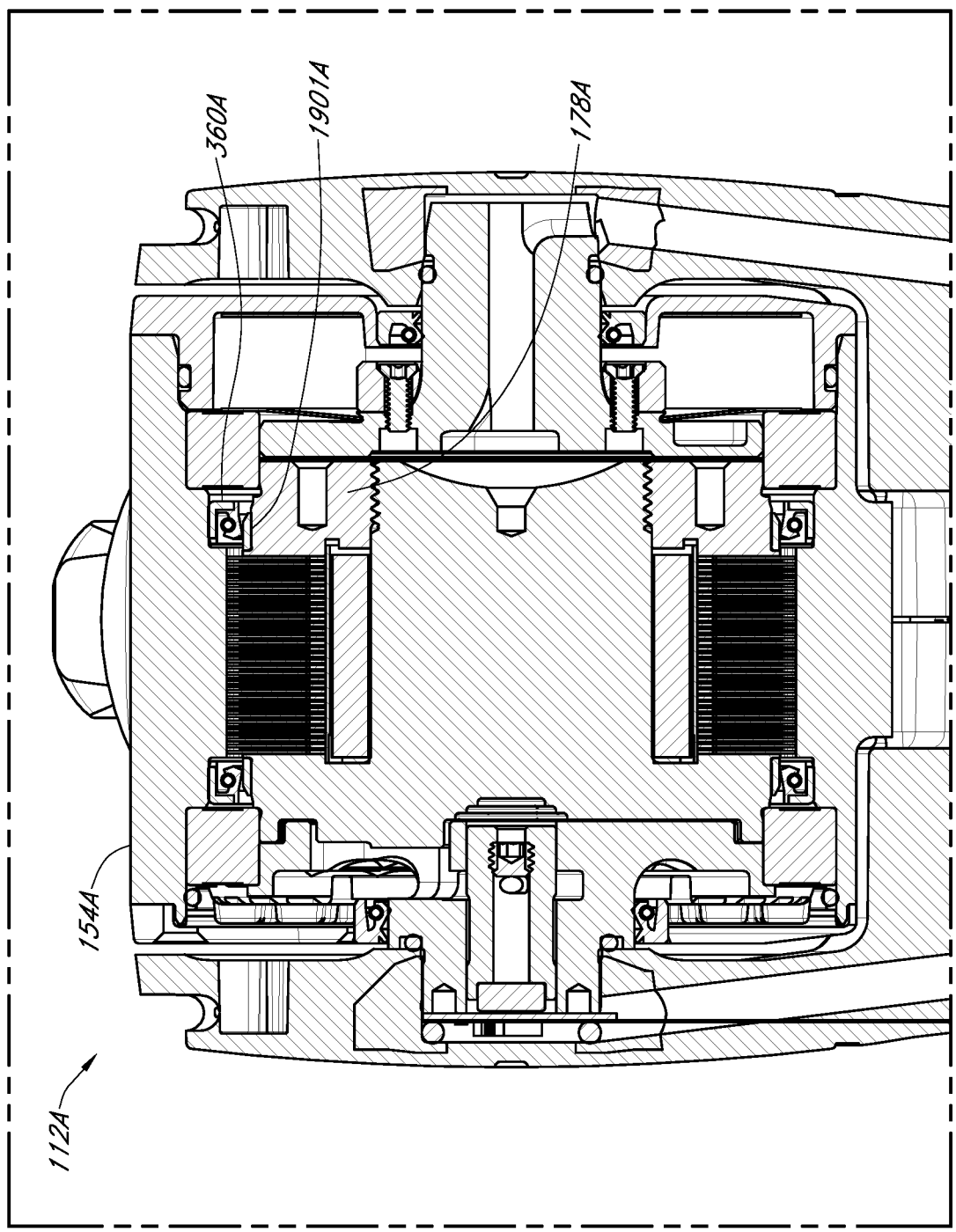
FIG. 19. is a cross-sectional side view of an upper portion of the prosthetic knee of FIG. 17 in the medial-lateral direction.

FIG. 19 depicts a cross-sectional view of the head of the knee actuator 112A for the prosthetic knee 110A. Metal sleeves 1901 are located between the core 178 and the dynamic seal assembly 360. The metal sleeves 1901 can be made from steel, and advantageously provide a wear-resistant surface for the sealing function of the dynamic seal assembly 360.

D. Coil Geometry

Figure 14:
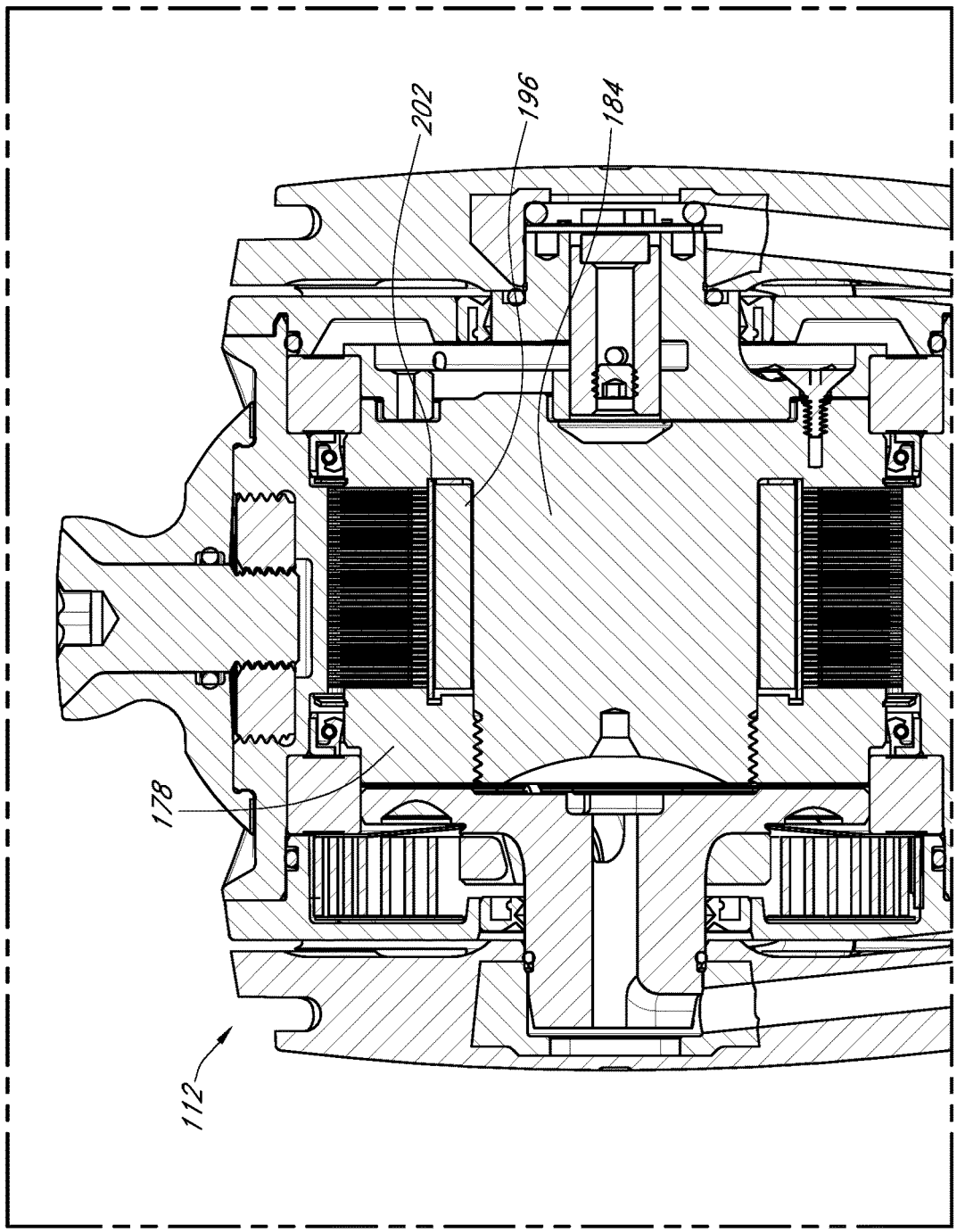
FIG. 14 is a cross-sectional view of a magnetorheological actuator for a prosthetic knee.
Figure 15:
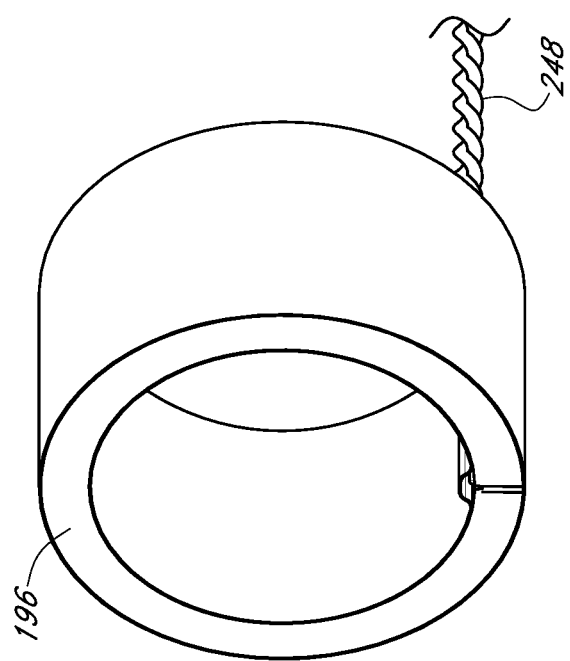
FIG. 15 is a perspective view of a coil of a magnetorheological actuator for a prosthetic knee.
Figure 16:
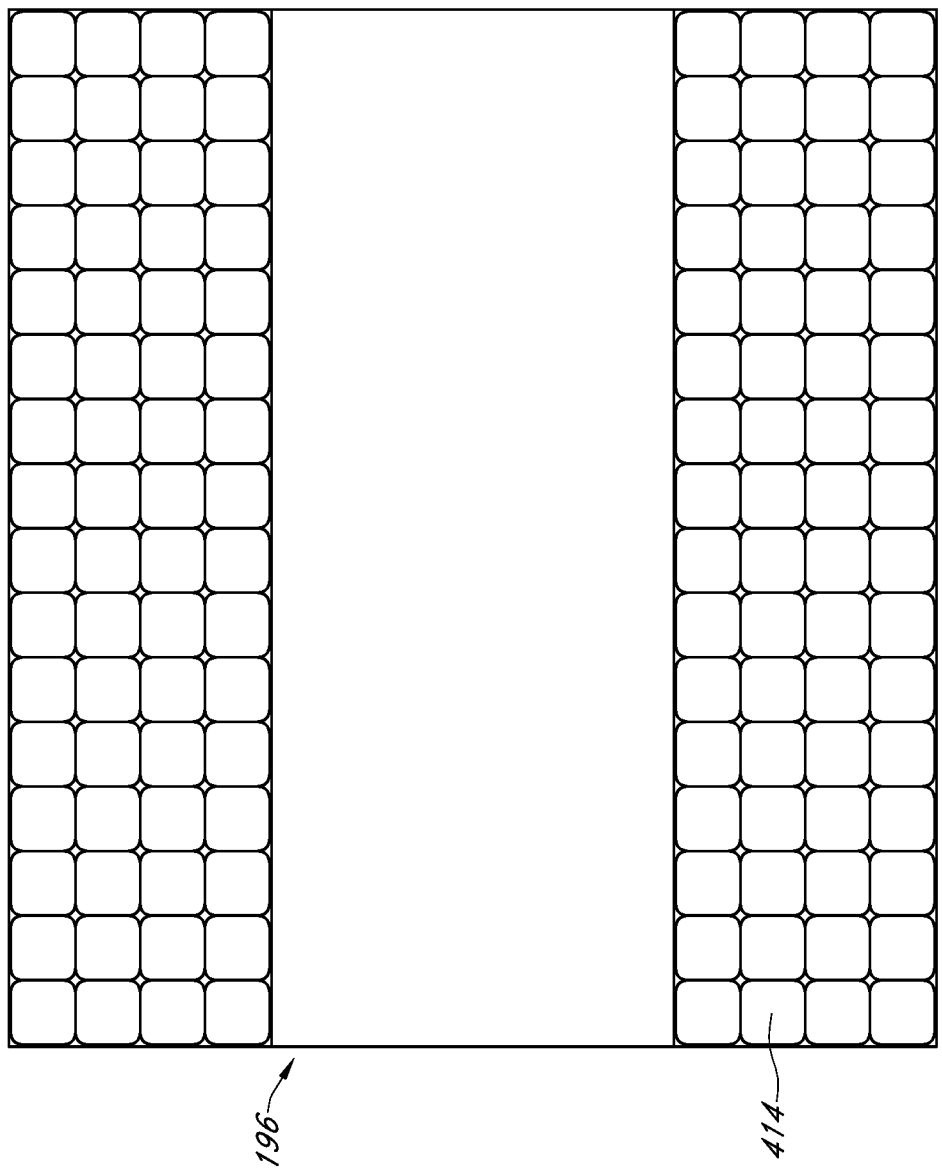
FIG. 16 is a schematic view of a cross-section of a coil of a magnetorheological actuator for a prosthetic knee.
Figure 17:
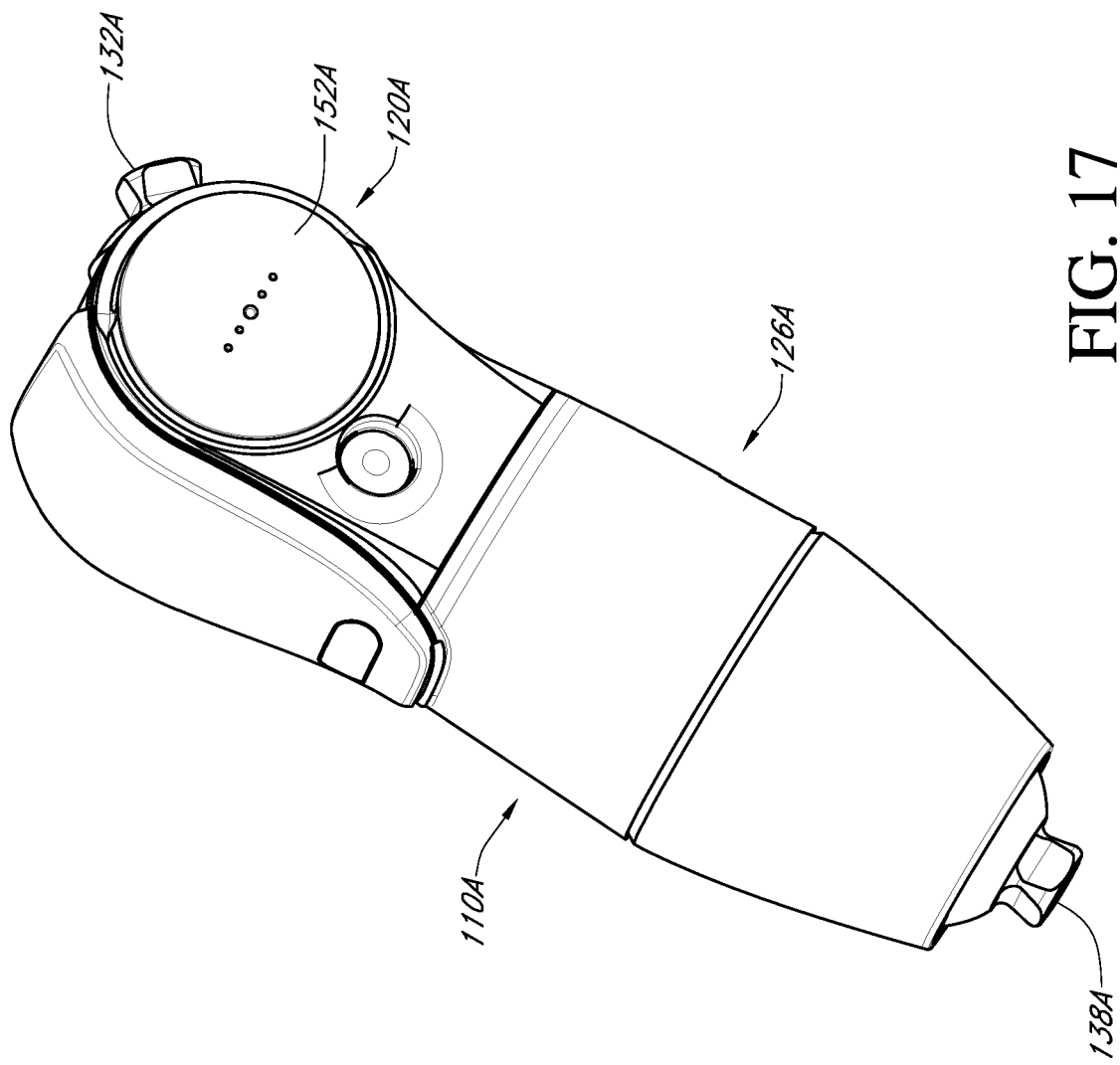
FIG. 17 is a perspective view of a prosthetic knee.
Figure 18:
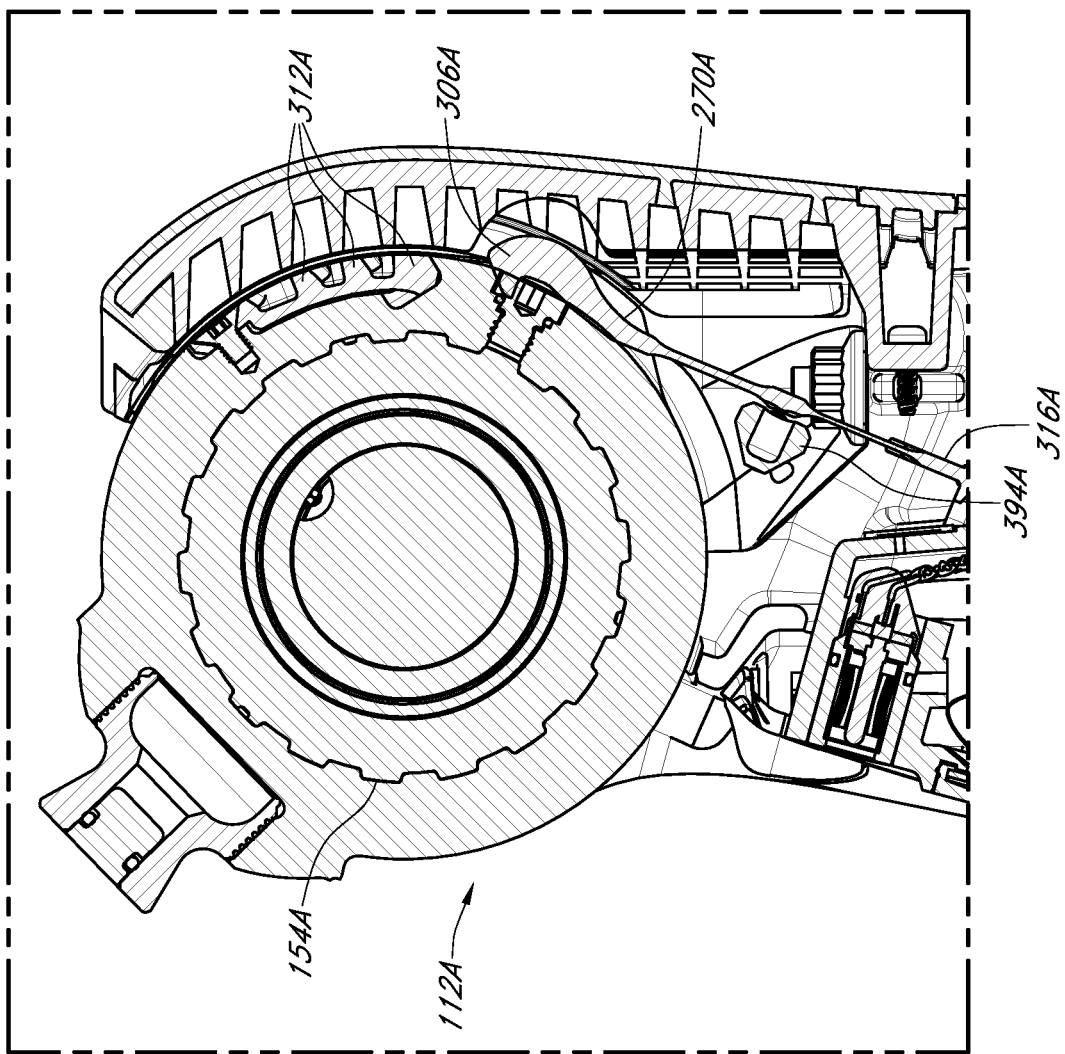
FIG. 18 is a cross-sectional side view of an upper portion of the prosthetic knee of FIG. 17 in the anterior-posterior direction.

FIGS. 14-16 depict the electromagnet coil 196 of the knee actuator 112. The electromagnet coil 196 can be located between the shank 204 of the screw component 184 of the core and the sheath 202. As depicted in FIG. 15, the coil 196 can have a lead wire 248. The wire 248 can protrude from an inner face of the coil 196. As previously discussed, the wire 248 can extend along the channel 242 in the screw component 184.

FIG. 16 shows a cross-sectional schematic view of the electromagnet coil 196. The windings 414 on the electromagnet coil 196 can have square or rectangular crosssections. In some embodiments, the windings 414 can be produced by flattening wire with an originally circular cross section. The windings 414 can be rectangular with round edges. In some embodiments, windings 414 can be produced by flattening wire from a circular cross-section to a generally rectangular cross-section with round edges. The cross-section of the windings 414 can allow the coil 196 to have higher fill factor compared to a coil with made up of wire with a circular cross-section. Though the coil 196 has rectangular shape windings with round edges in the illustrated embodiment, in other implementations the coil 196 can have windings with other suitable non-circular cross-sectional shapes that allow for a higher fill factor, such as coils 196 that have windings with one or more linear edges that can be arranged adjacent to a linear edge of an adjacent winding.

The higher fill factor can be advantageous to obtain increased magnetic field with the same volume of coil because more windings can be filled into the same space. The result of more windings is a more powerful electromagnet coil 196. With more windings, as compared to a coil using circular wire, less current is required to get the same electric motor force. Advantageously, the higher fill factor provides either more braking or less current for same torque. The high fill factor coil 196 can use less power to generate the same magnetic field as compared to a coil using circular wire.

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel"

refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

Of course, the foregoing description is that of certain features, aspects and advantages of the present invention, to which various changes and modifications can be made without departing from the spirit and scope of the present invention. Moreover, the devices described herein need not feature all of the objects, advantages, features and aspects discussed above. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed devices.

What is claimed is:

1. A prosthetic knee, comprising:
    an elongate frame configured to house electronics;
    a magnetorheological (MR) fluid actuator movably coupled to a proximal portion of the elongate frame, the actuator being rotatable in an anterior-posterior direction about a medial-lateral axis, the actuator comprising an outer spline and a core assembly;
    a lock assembly operable to lock the actuator relative to the frame in one or more extension positions, the lock assembly comprising:
        a blade, having a flexible distal portion, the blade configured to move in an anterior-posterior direction perpendicular to the medial-lateral axis, and
        one or more teeth on the outer spline, between a medial side and a lateral side of the actuator, the one or more teeth configured to releasably engage the blade to lock the actuator, the blade having a hook that engages the one or more teeth;
    a coil;
    a proximal connector coupled to the outer spline and configured to rotate with the outer spline about the medial-lateral axis; and
    a distal connector coupled to a distal end of the elongate frame,
    wherein a torsional resistance of the actuator to rotation about the medial-lateral axis varies based on a magnitude of a magnetic field applied by the coil to the magnetorheological fluid to vary a viscosity of the MR fluid in the actuator.

2. The prosthetic knee of claim 1, wherein the core assembly comprises a core extending from a first plate attached to the core.

3. The prosthetic knee of claim 2, wherein the actuator further comprises a second plate removably coupleable to an opposite end of the core from the first plate.

4. The prosthetic knee of claim 2, wherein the coil is disposed about the core.

5. The prosthetic knee of claim 3, wherein the actuator further comprises a collar disposed about the coil and coupled to the first and second plates, the collar having a continuous outer surface with an outer dimension.

6. The prosthetic knee of claim 5, wherein the actuator further comprises a first plurality of annular blades slideable over the collar and having an opening with an inner dimension approximately equal to the outer dimension of the collar.

7. The prosthetic knee of claim 6, wherein the actuator further comprises a second plurality of annular blades slideable over the collar and having a toothed outer edge that define one or more teeth configured to engage with a splined surface of the outer spline, each of the second plurality of annular blades alternating with and separated from each of the first plurality of annular blades by a gap containing a magnetorheological fluid, the first plurality of annular blades being clamped between the first and second plates.

8. The prosthetic knee of claim 6 further comprising a plurality of annular spacers, each spacer positioned between two blades of the first plurality of annular blades.

9. The prosthetic knee of claim 3, wherein the second plate is threadably coupled to the core.

10. The prosthetic knee of claim 1, wherein the coil is a compact coil comprising one or more wire portions, each wire portion having a transverse cross-section defined by one or more linear surfaces configured to be adjacent a linear surface of an adjacent wire portion.

11. The prosthetic knee of claim 10, wherein the cross-section is rectangular.

12. The prosthetic knee of claim 11, wherein the cross-section is square.

13. The prosthetic knee of claim 1 further comprising a seal assembly between the outer spline and the core, the seal assembly comprising a cavity filled with grease.

14. The prosthetic knee of claim 1, wherein the blade is actuatable to disengage the teeth to allow the actuator to rotate.

15. The prosthetic knee of claim 14, wherein the blade is actuatable via a lock toggle assembly that includes a wheel movably mounted on a shaft, the wheel configured to engage first and second indents of the blade as the shaft is moved in a transverse direction relative to the blade, wherein when the wheel engages the first indent the blade is deflected outward to disengage the teeth to allow rotation of the actuator, and wherein when the wheel engages the second indent the blade is moved to engage the teeth to lock a position of the actuator.

16. A prosthetic knee, comprising:
    an elongate frame configured to house electronics;
    a magnetorheological (MR) fluid actuator movably coupled to a proximal portion of the elongate frame, the actuator being rotatable in an anterior-posterior direction about a medial-lateral axis, the actuator comprising an outer spline and a core assembly;
    a coil comprising one or more wire portions, each wire portion having a transverse cross-section defined by one or more linear surfaces configured to be adjacent a linear surface of an adjacent wire portion;

a lock assembly operable to lock the actuator relative to the frame in one or more extension positions, the lock assembly comprising:
   a blade, having a flexible distal portion, and
   one or more teeth on the outer spline, the one or more teeth configured to releasably engage the blade to lock the actuator, the blade having a hook that engages the one or more teeth;
a proximal connector coupled to the outer spline and configured to rotate with the outer spline about the medial-lateral axis; and
a distal connector coupled to a distal end of the elongate frame,
wherein a torsional resistance of the actuator to rotation about the medial-lateral axis varies based on a magnitude of a magnetic field applied by the coil to the magnetorheological fluid to vary a viscosity of the MR fluid in the actuator.

17. The prosthetic knee of claim 16, wherein the cross-section is rectangular.

18. The prosthetic knee of claim 17, wherein the cross-section is square.

19. The prosthetic knee of claim 16, wherein the blade is actuatable via a lock toggle assembly that includes a wheel movably mounted on a shaft, the wheel configured to engage first and second indents of the blade as the shaft is moved in a transverse direction relative to the blade, wherein when the wheel engages the first indent the blade is deflected outward to disengage the teeth to allow rotation of the actuator, and wherein when the wheel engages the second indent the blade is moved to engage the teeth to lock a position of the actuator.

* * * * *